(12) United States Patent
Lombardi et al.

(10) Patent No.: US 9,115,138 B2
(45) Date of Patent: Aug. 25, 2015

(54) PORPHYRIN COMPOUNDS COMPRISING ONE OR MORE PYRIDONE MOIETIES

(71) Applicant: Ventana Research Corporation, Tucson, AZ (US)

(72) Inventors: John L. Lombardi, Tucson, AZ (US); Chuchawin Changtong, Tucson, AZ (US)

( * ) Notice: Subject to any disclaimer, the term of this patent is extended or adjusted under 35 U.S.C. 154(b) by 0 days.

(21) Appl. No.: 13/899,468

(22) Filed: May 21, 2013

(65) Prior Publication Data

US 2013/0324714 A1     Dec. 5, 2013

Related U.S. Application Data

(62) Division of application No. 12/245,614, filed on Oct. 3, 2008, now Pat. No. 8,445,683.

(51) Int. Cl.
    *C07D 401/00*     (2006.01)
    *A01N 43/40*     (2006.01)
    *A61K 31/44*     (2006.01)
    *C07D 487/22*     (2006.01)
    *C07D 519/00*     (2006.01)

(52) U.S. Cl.
    CPC ............ *C07D 487/22* (2013.01); *C07D 519/00* (2013.01)

(58) Field of Classification Search
    CPC ............................... A01N 43/40; C07D 211/94
    USPC ................. 514/410, 338; 548/419; 546/276.7
    See application file for complete search history.

(56) References Cited

PUBLICATIONS

De Luca et. al., Journal of Physical Chemistry B, 2006, American Chemical Society, vol. 110, pp. 14135-14141.*
Rothemund et. al., JACS, 1941, American Chemical Society, vol. 63, pp. 267-270.*

* cited by examiner

*Primary Examiner* — Sarah Pihonak
(74) *Attorney, Agent, or Firm* — Dale F. Regelman; Quarles & Brady LLP

(57) ABSTRACT

Various porphyrin compounds comprising one or more pyridone moieties, intermediates thereof, compositions thereof, and, methods of making and using thereof.

1 Claim, 22 Drawing Sheets

¹H-NMR SPECTRUM OF PORPHYRIN 130

$^1$H-NMR SPECTRUM OF PORPHYRIN 140

$^1$H-NMR SPECTRUM OF PORPHYRINS 1330 AND 1340

FIG. 17

| Compound | $\Delta H^{\neq}$(kcal/mol) | $\Delta S^{\neq}$(cal/mol K) | $\Delta G^{\neq}$(kcal/mol) |
|---|---|---|---|
| Porphyrin 140 | 26.73±0.47 | 9.05±1.50 | 24.03±0.02 |
| Endoperoxide 1010 | 26.30±0.05 | 6.89±0.16 | 24.20±0.05 |
| Porphyrin 1430 and 1440 | 25.30±2.80 | 3.41±8.90 | 24.30±2.60 |
| Porphyrin 1430 and 1440 Endoperoxides | 26.40±1.18 | 5.89±3.70 | 24.60±1.10 |

PORPHYRIN COMPOUNDS COMPRISING ONE OR MORE PYRIDONE MOIETIES

CROSS REFERENCE TO RELATED APPLICATIONS

This application is a Divisional application claiming priority from U.S. Nonprovisional application Ser. No. 12/245,614 filed on Oct. 3, 2008, now U.S. Pat. No. 8,445,683, which is incorporated by reference herein.

STATEMENT OF GOVERNMENT INTEREST

Not applicable.

BACKGROUND OF THE INVENTION

Exposure to pathogens, such as and without limitation toxic chemical and biological agents, is a growing concern to both military and civilian organizations alike. Areas of enhanced vulnerability include assemblies of persons, whether military or civilian. One such scenario includes military personnel assembled within one or more tents and/or portable shelters.

U.S. Pat. No. 7,259,122 (the '122 patent) teaches that singlet oxygen may be used to decontaminate a wide variety of pathogens. The '122 patent further teaches use of a photocatalyst to generate singlet oxygen from ambient oxygen, in combination with a singlet oxygen trap.

SUMMARY OF THE INVENTION

One aspect of the invention is a compound according to the structure

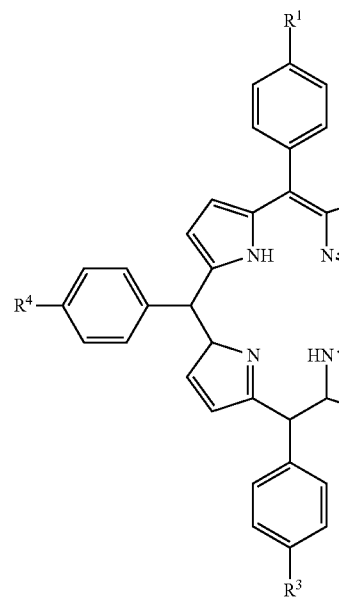

wherein $R^1$, $R^2$, $R^3$ and $R^4$ are

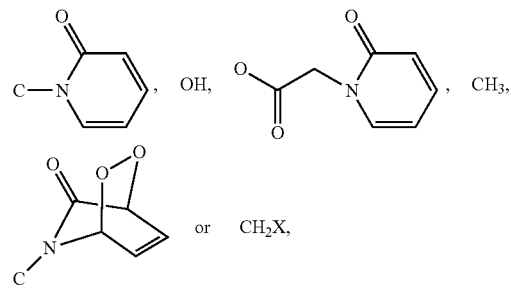

and, wherein X is Cl, Br or I; or, a salt, solvate or hydrate thereof.

In an exemplary embodiment, the compound has the following structure

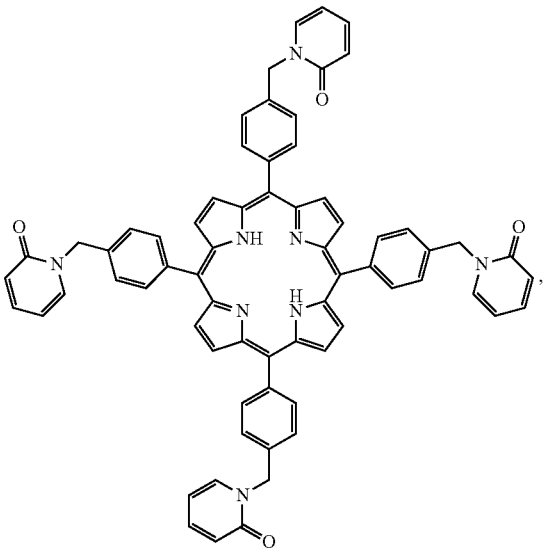 [SMILES: O=c1ccccn1Cc1ccc(-c2c3nc(c(-c4ccc(Cn5ccccc5=O)cc4)c4ccc([nH]4)c(-c4ccc(Cn5ccccc5=O)cc4)c4nc(c(-c5ccc(Cn6ccccc6=O)cc5)c5ccc2[nH]5)C=C4)C=C3)cc1]

or, a salt, solvate or hydrate thereof.

In another exemplary embodiment, the compound has the following structure

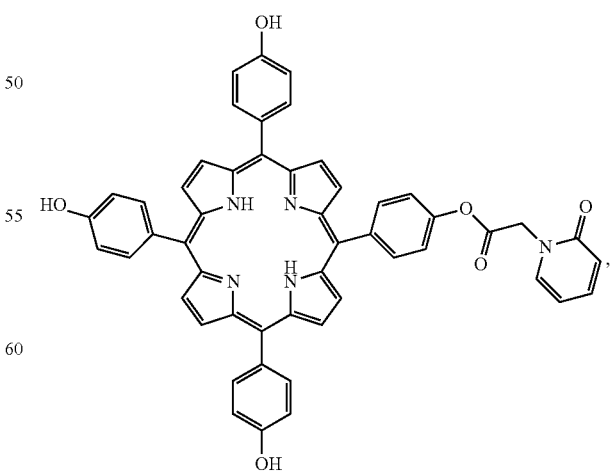

or, a salt, solvate or hydrate thereof.

In another exemplary embodiment, the compound has the following structure

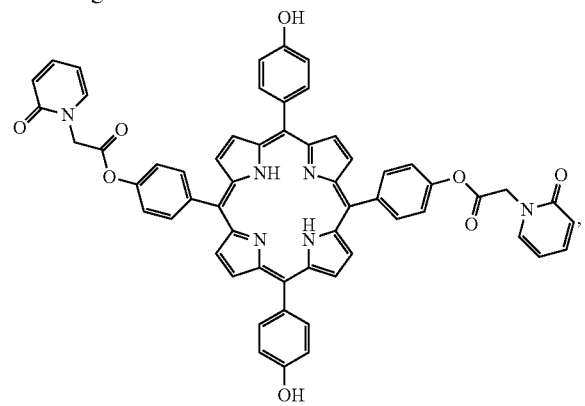

or, a salt, solvate or hydrate thereof.

In another exemplary embodiment, the compound has the following structure

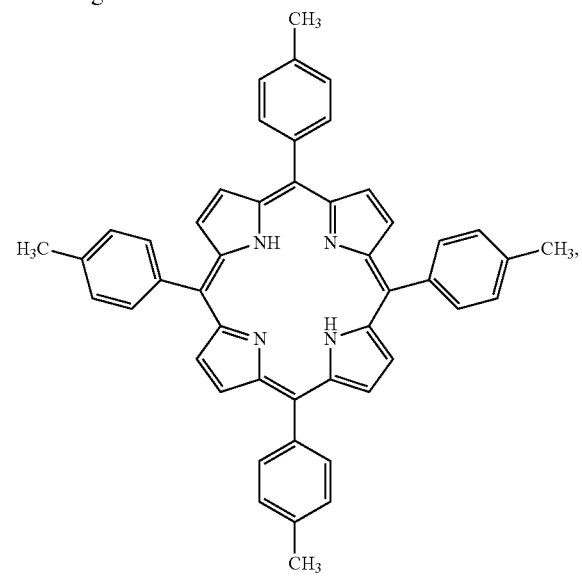

or, a salt, solvate or hydrate thereof.

In another exemplary embodiment, the compound has the following structure

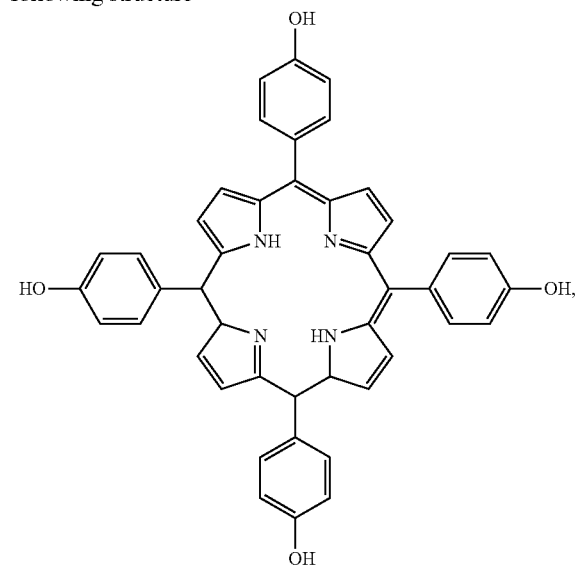

or, a salt, solvate or hydrate thereof.

In another exemplary embodiment, the compound has the following structure

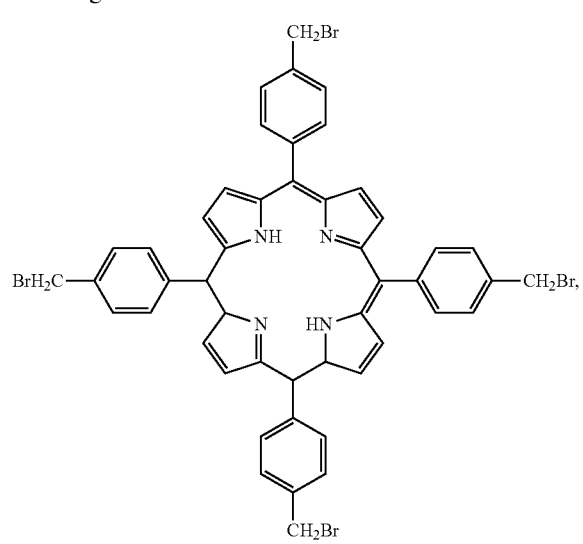

or, a solvate or hydrate thereof.

In another exemplary embodiment, the compound has the following structure

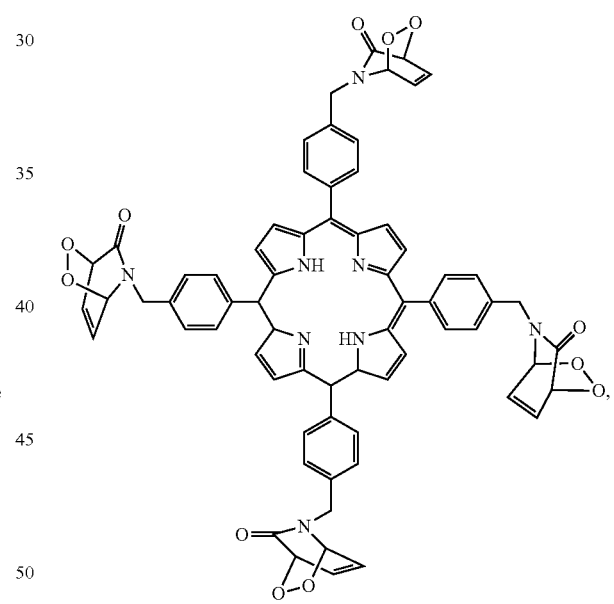

or, a salt, solvate or hydrate thereof.

Another aspect of the invention is a composition comprising any one of the above compounds above, an N-substituted-2-pyridone, and, a photocatalyst.

Another aspect of the invention is a method of decontaminating one or more pathogens, with or without ambient light, comprising the steps or acts of providing one or more pathogens in an ambient oxygen-containing atmosphere and providing the above composition.

Another aspect of the invention is a method of making any one of the above compounds comprising the steps or acts of providing a core-containing compound according to the structure

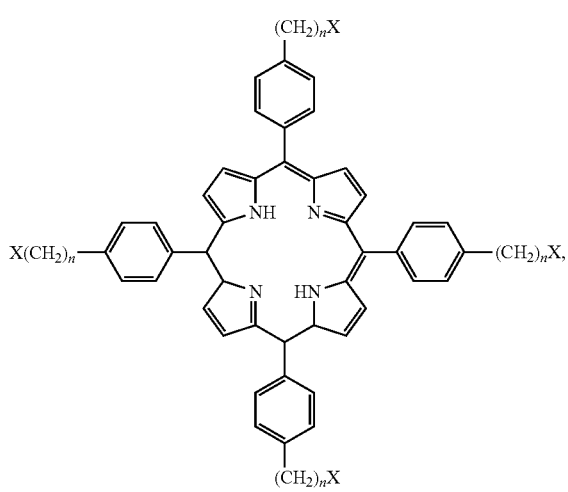

wherein n is 1, 2 or 3, and, wherein X is Cl, Br or I, covalently bonding the core-containing compound with a substituted pyridone according to the structure

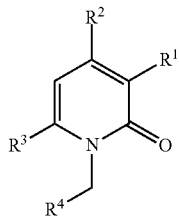

to produce a product, wherein $R^1$ is H, $CH_3$, $OCH_3$ or $(CH_3)_2N$, wherein $R^2$ is H or $CH_3$, wherein $R^3$ is H, $CH_3$, $OCH_3$, or $(CH_3)_2N$, and, wherein $R^4$ is Ph, p-CNPh, $CH_2(CH_2)_4CH_3$, $COCH_2CH_3$, OH or COOH, and, reacting the substituted pyridone with $O_2$ to yield an endo peroxide according to the structure

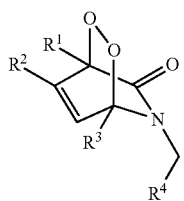

BRIEF DESCRIPTION OF DRAWINGS OF THE EXEMPLARY EMBODIMENTS

FIG. 1 is an illustration showing molecular oxygen in its ground state containing two unpaired electrons and resides in a triplet spin state, whereby singlet oxygen is an excited form in which all electrons are paired, whereby the first excited singlet state of oxygen is 22 kcal/mol above its ground state, whereby the singlet oxygen is a reactive oxidant, and, whereby generation of singlet oxygen by energy transfer from a photosensitizer is shown.

FIG. 2 shows a chemical reaction, whereby porphyrin 130 was prepared from starting materials 110 and 120 utilizing three acid catalysts being $BF_3$-etherate, trifluoroacetic acid ("TFA"), and amberlyst ion-exchange resin.

FIG. 3 shows a chemical reaction, whereby tetra pyridone substituted porphyrin 140 was prepared from porphyrin 130.

FIG. 4A shows the $^1$H-NMR spectrum for porphyrin 130.
FIG. 4B shows the $^1$H-NMR spectrum for porphyrin 140.
FIG. 5 shows the UV-Vis absorption overlay spectrum between the porphyrin 140 and tetra-(4-methylphenyl)porphyrin ("T4mPP") in chloroform solvent.

FIG. 6 shows the fluorescence emission of the porphyrin 140, which was similar to the emission of T4mPP.

FIG. 7 shows the UV-Vis absorption overlay spectrum of the porphyrin 140 solution in chloroform before and after 5 and 15 min of irradiation.

FIG. 8 shows the UV-Vis absorption overlay spectrum of a solution of T4mPP in chloroform before and after 10 min of irradiation, whereby FIGS. 7 and 8 demonstrate that the efficiency of porphyrin 140 as a photocatalyst is not diminished by the presence of the 4 pyridone moieties.

Figure 11A:
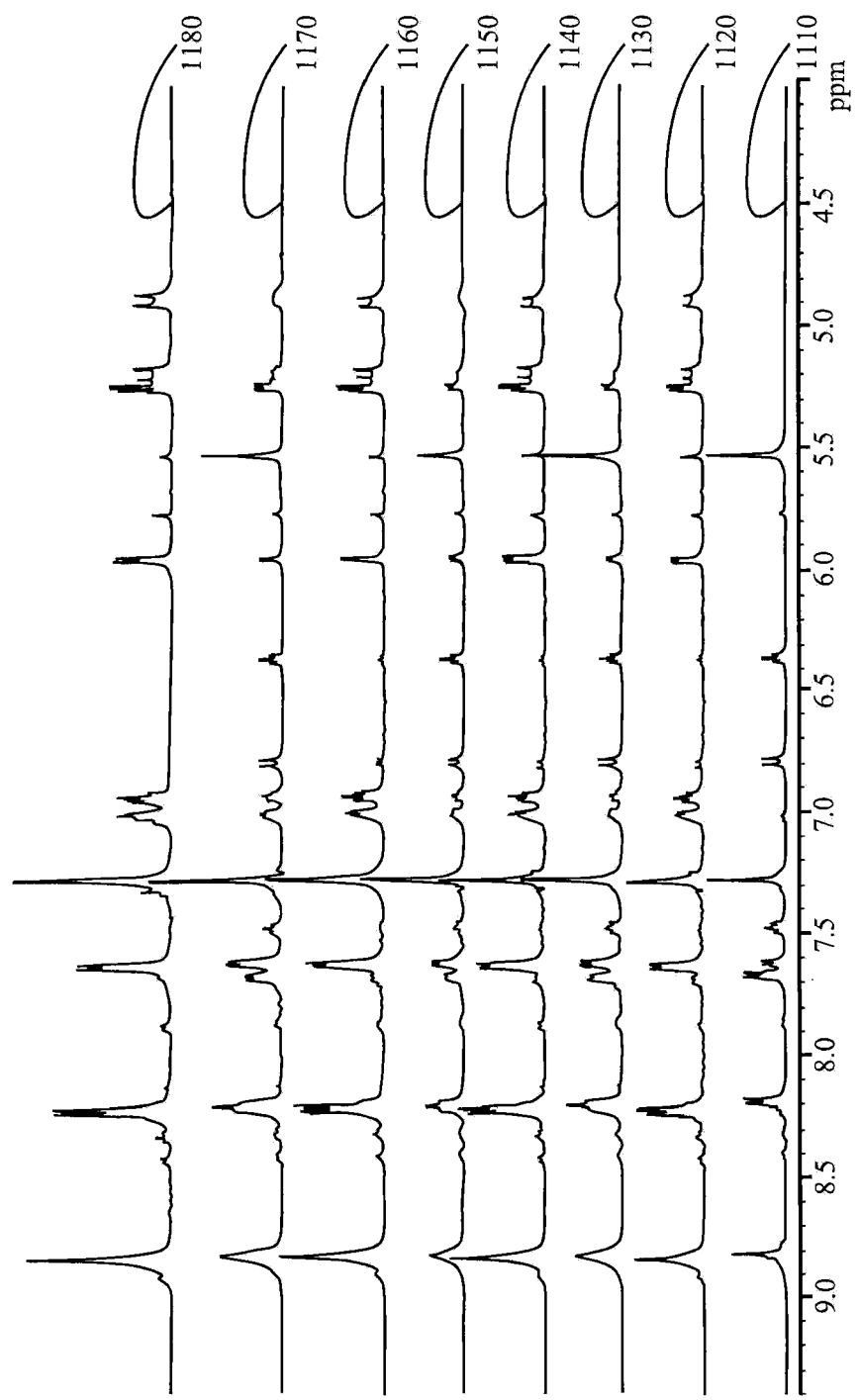
FIG. 11A shows the $^1$H-NMR overlay spectrum of the porphyrin 140 solution in $CDCl_3$ before and after irradiation through a yellow filter.
Figure 11B:
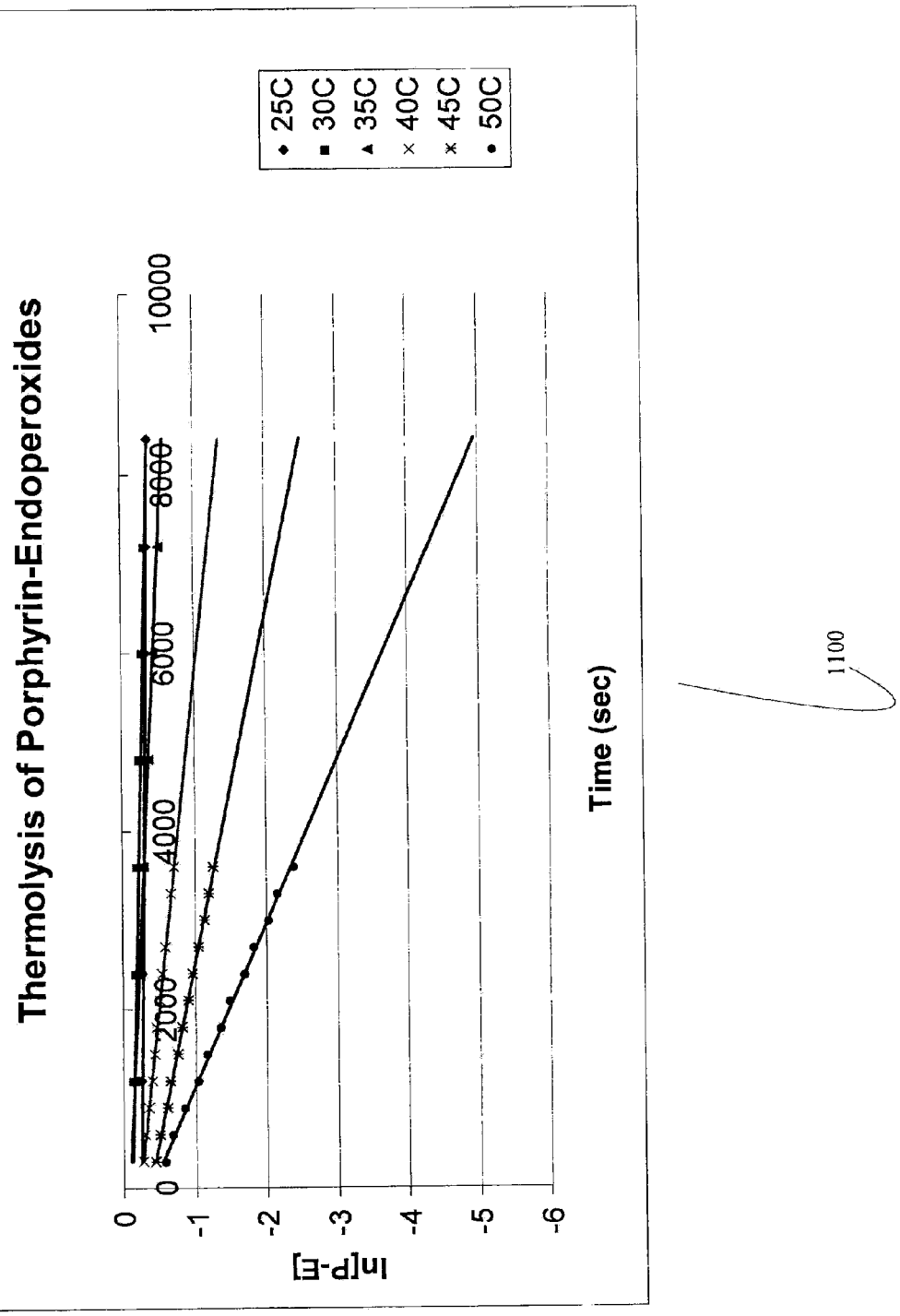

FIG. 11B graphically illustrates the thermolysis data for porphyrin endoperoxide 1010.

Figure 11C:
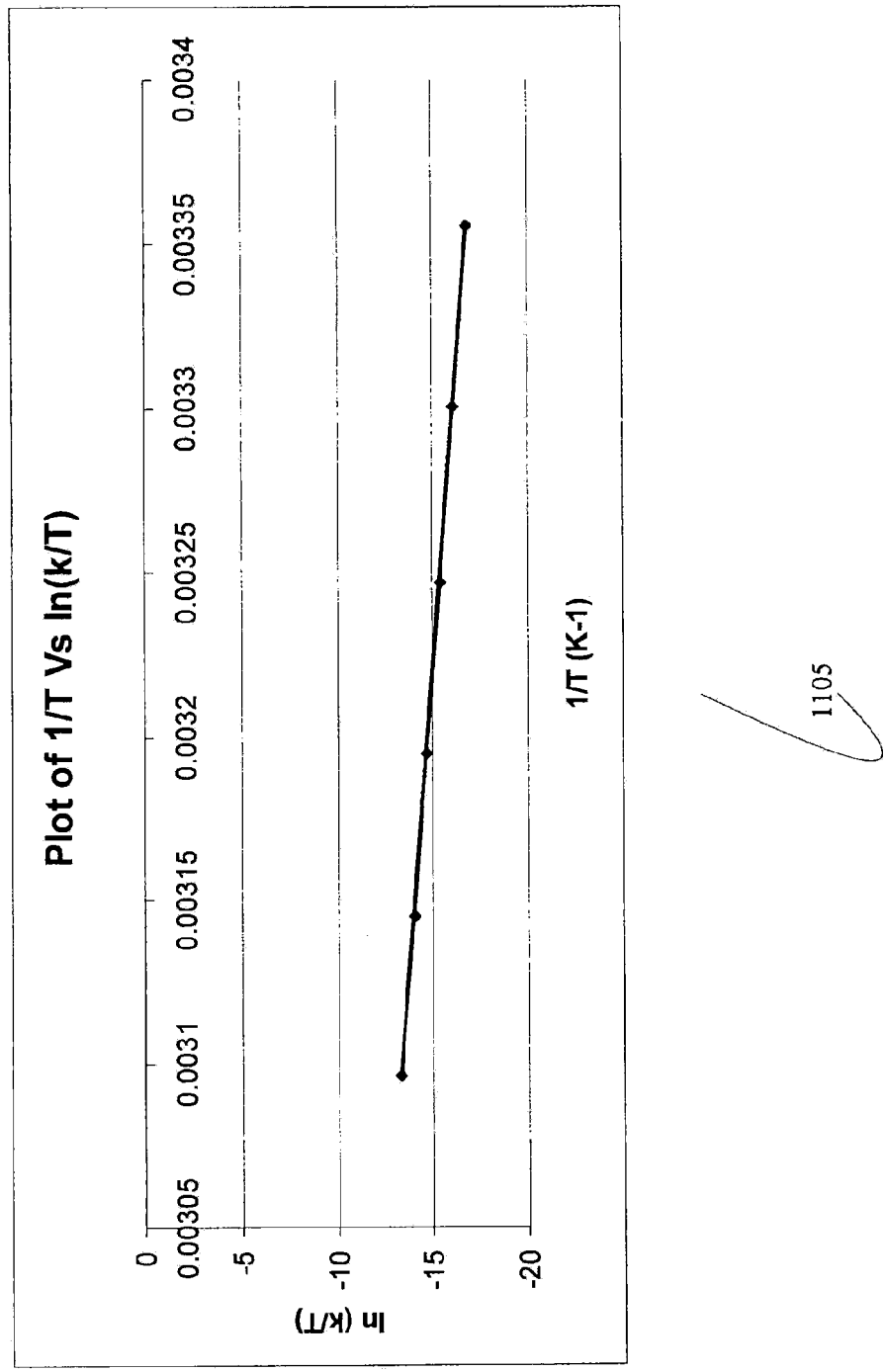

FIG. 11C graphically illustrates 1/T Vs. ln(k/T) from the thermolysis of the porphyrin endoperoxide 1010.

Figure 12:
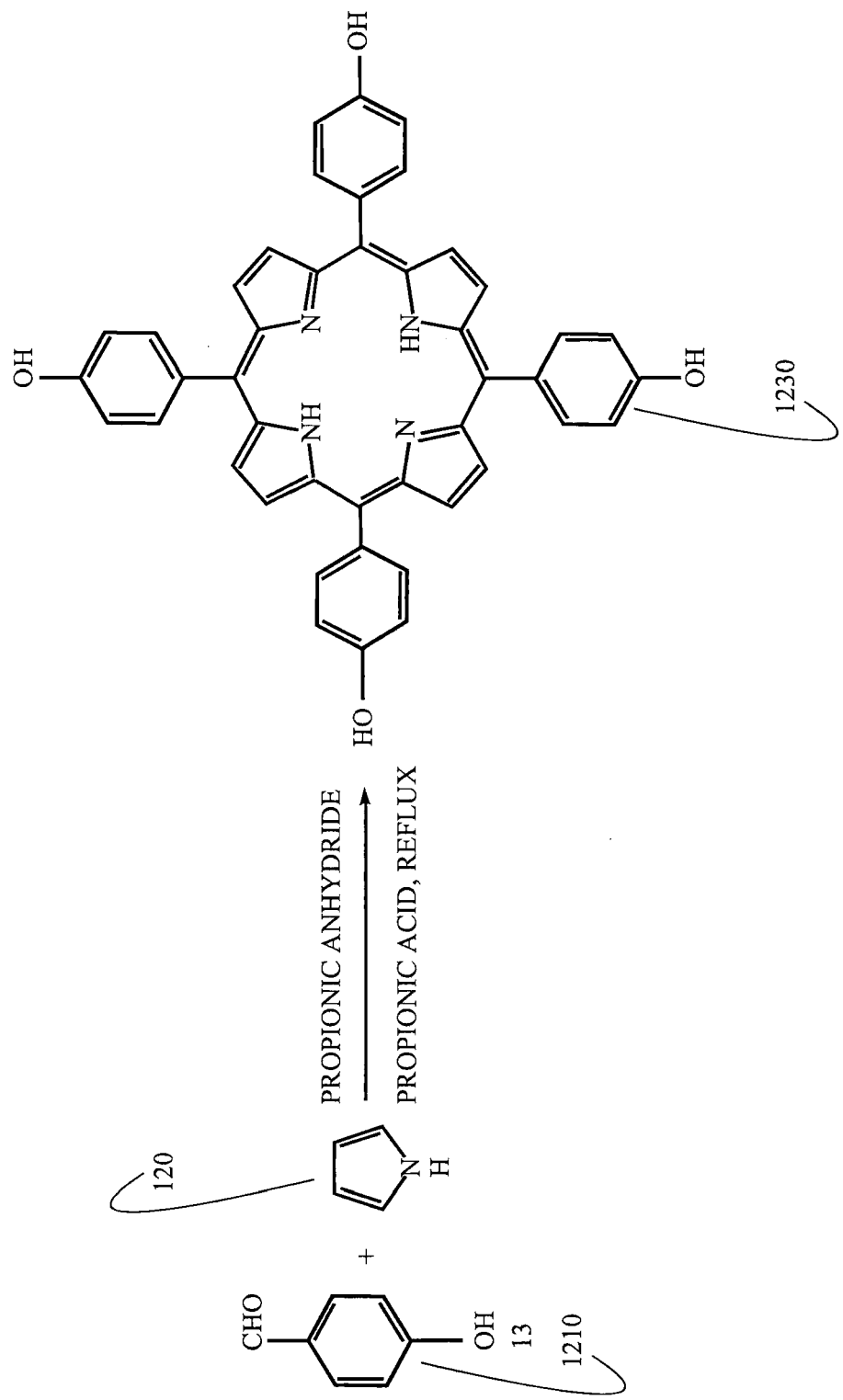

FIG. 12 shows the chemical reaction to make porphyrin 1230 from starting materials 1210 and 120 utilizing propionic anhydride and propionic acid.

Figure 13:
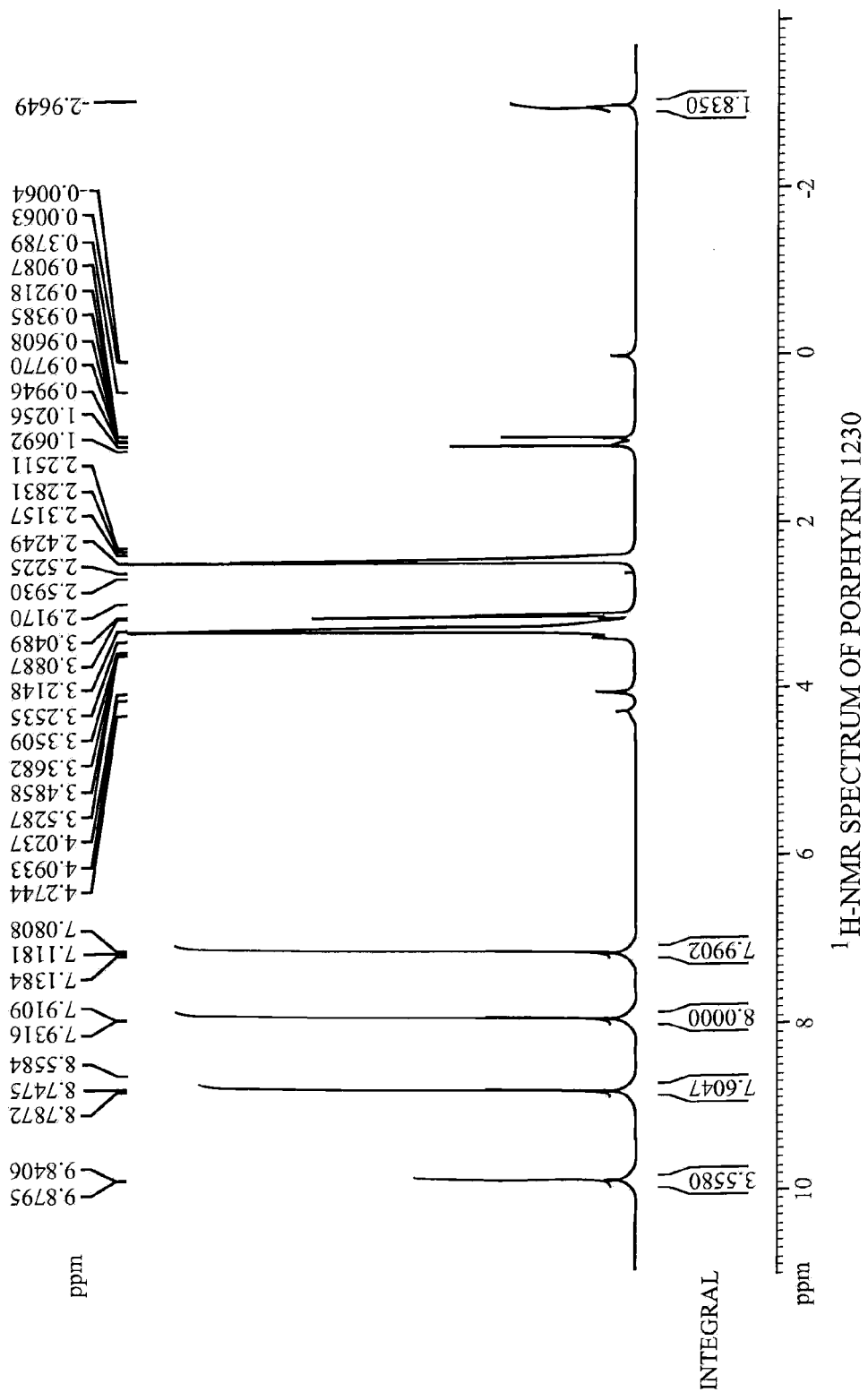

FIG. 13 shows the $^1$H-NMR spectrum for porphyrin 1230.

Figure 14:
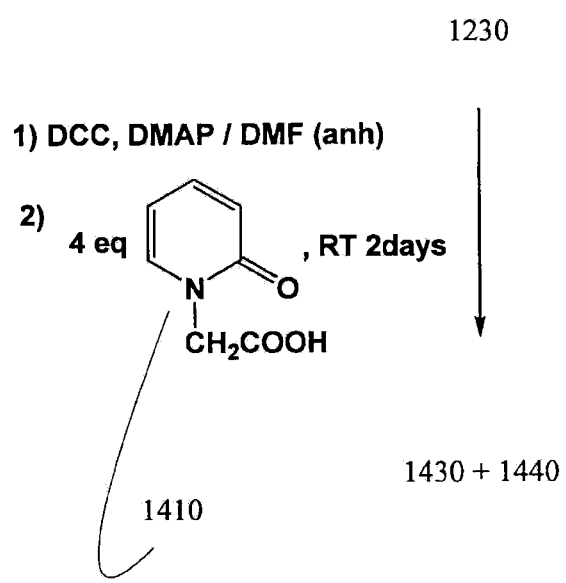

FIG. 14 shows the preparation of mono- and di-substituted porphyrins 1420 and 1430 from porphyrin 1230 and substituted pyridone 1410.

Figure 15:
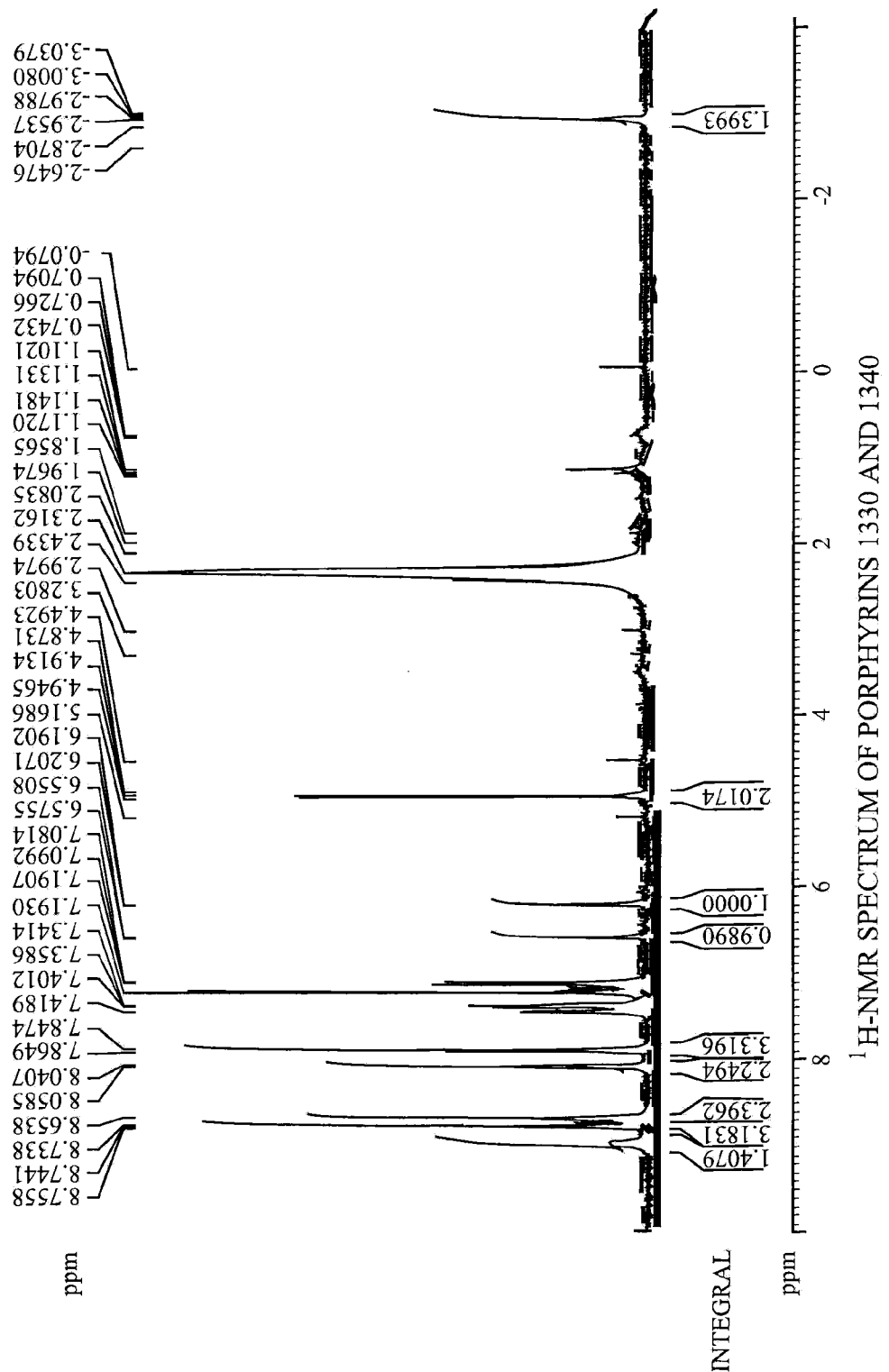

FIG. 15 is the $^1$H-NMR spectrum of porphyrins 1330 and 1340.

Figure 16A:
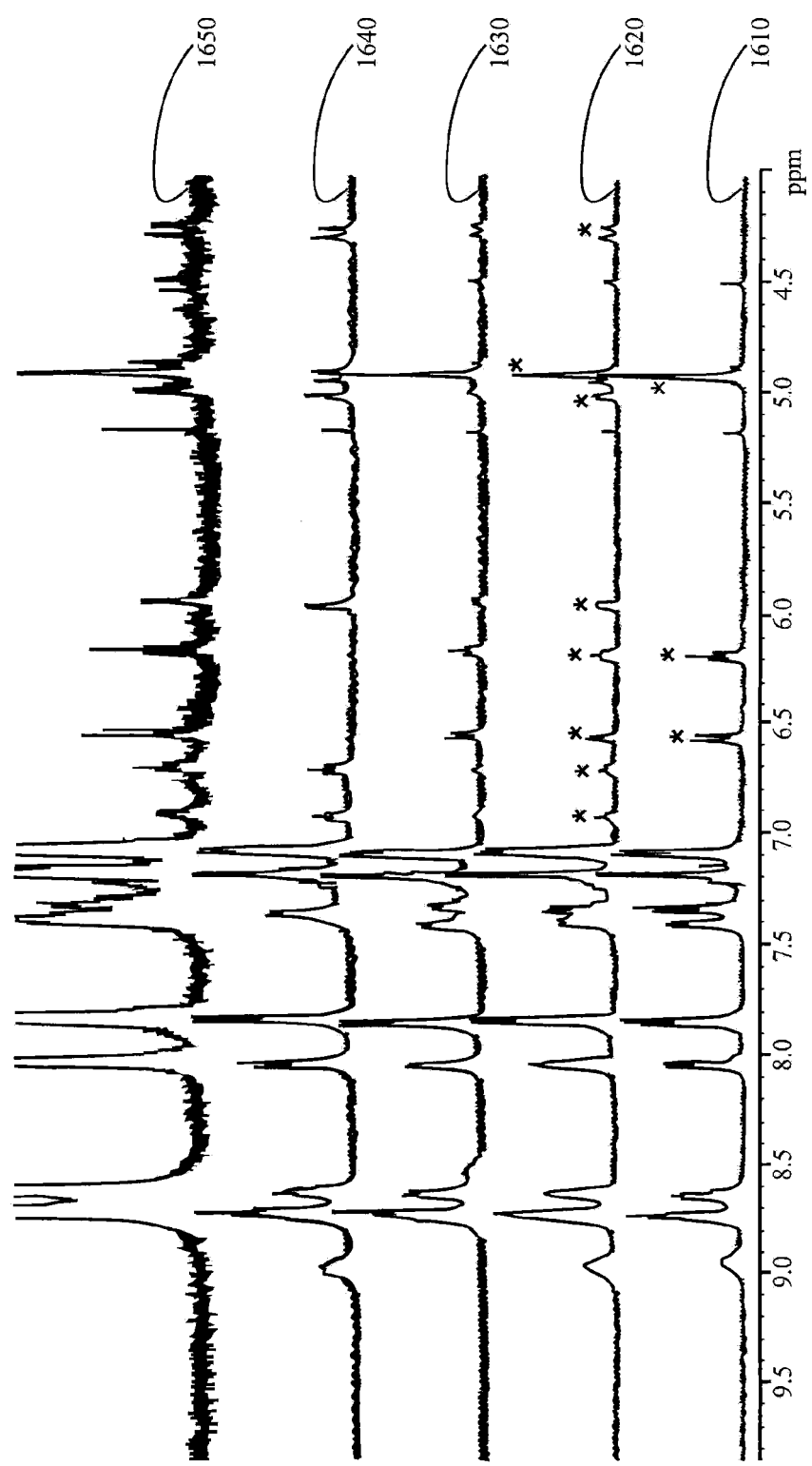

FIG. 16A comprises a $^1$H-NMR overlay spectrum of the porphyrins 1430 and 1440 solution in $CDCl_3$ before and after irradiation through a yellow filter.

Figure 16B:
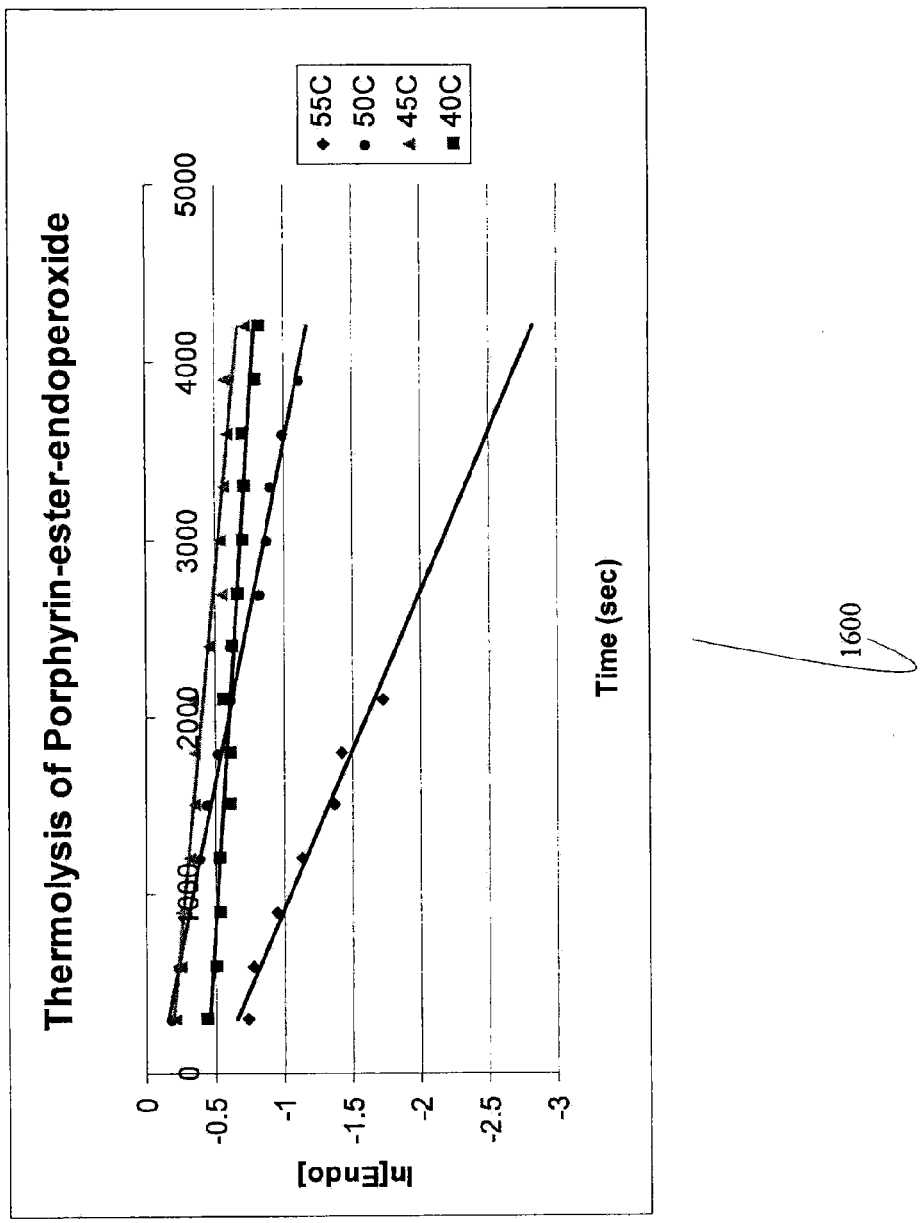

FIG. 16B graphically illustrates the thermolysis data for porphyrin endoperoxides formed from the mixture of pyridone/porphyrins 1430 and 1440.

Figure 16C:
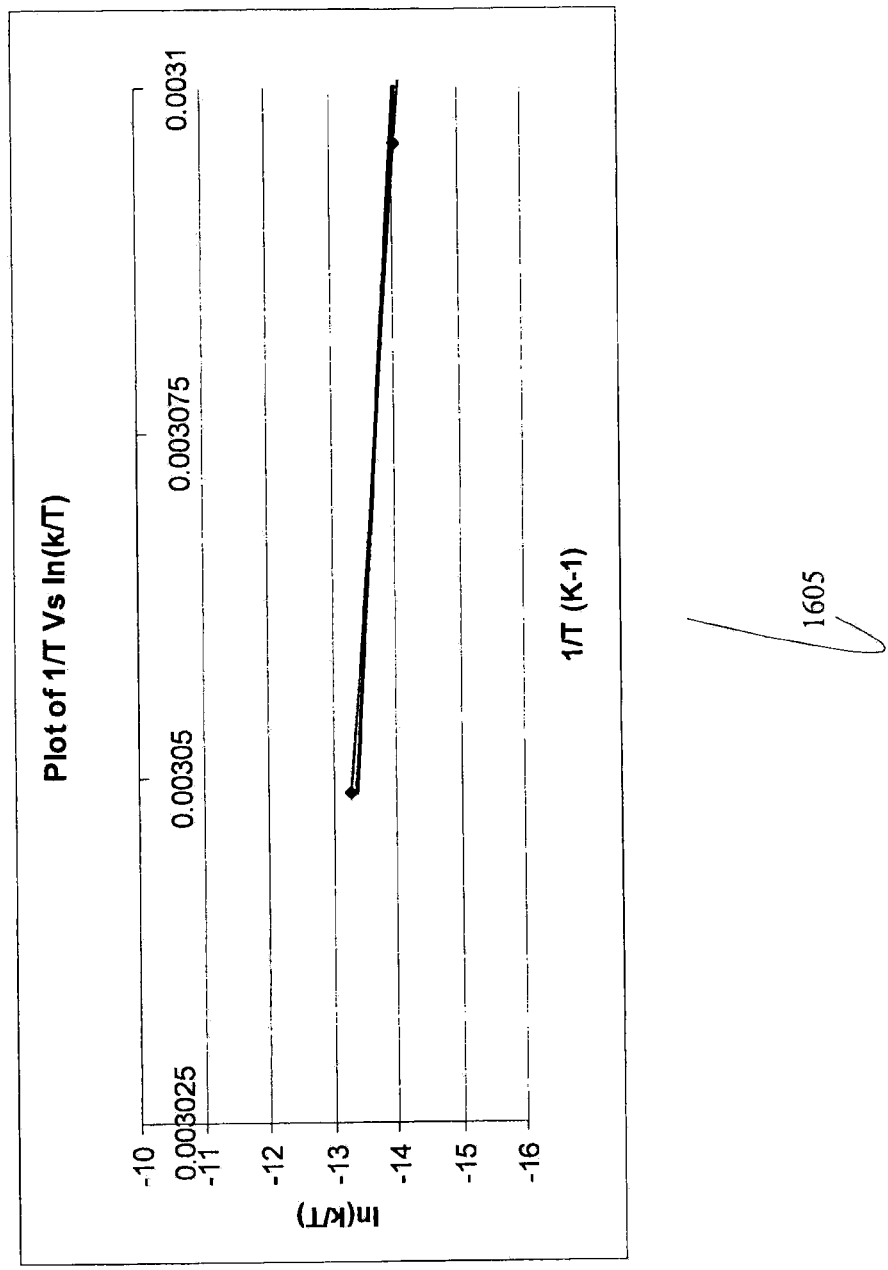

FIG. 16C graphically illustrates 1/T Vs. ln(k/T) from the thermolysis of the porphyrin endoperoxides formed from the mixture of pyridone/porphyrins 1430 and 1440.

FIG. 17 is a table illustrating the kinetic decomposition data for porphyrins 140/mixture 1430 and 1440, and the endoperoxides formed therefrom.

DETAILED DESCRIPTION OF THE EXEMPLARY EMBODIMENTS

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

U.S. Pat. No. 7,259,122 (the '122 patent), in the name of Lombardi, teaches that singlet oxygen may be used to decontaminate a wide variety of pathogens, and is hereby incorporated herein by reference in its entirety. The '122 patent further teaches use of a photocatalyst to generate singlet oxygen from ambient oxygen, in combination with a singlet oxygen trap.

Figure 1:
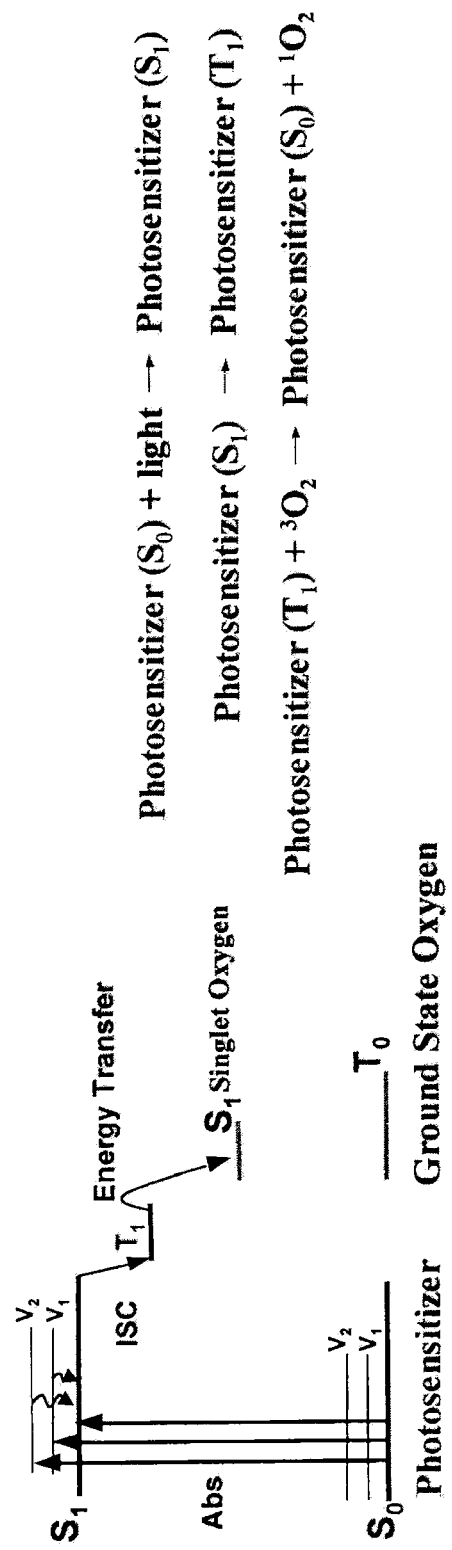

Referring to FIG. 1, molecular oxygen in its ground state contains two unpaired electrons and resides in a triplet spin state. Singlet oxygen is an excited form in which all electrons are paired. This first excited singlet state of oxygen is 22 kcal/mol above its ground state. Singlet oxygen is a reactive oxidant. Generation of singlet oxygen by energy transfer from a photosensitizer is shown in FIG. 1.

It is known in the art that polycyclic aromatic hydrocarbons (PAHs), such as for example diphenylanthracene 1, can reversibly react with singlet oxygen 2 to give endoperoxide adduct 3. Decomposition of these endoperoxides upon heating releases singlet oxygen.

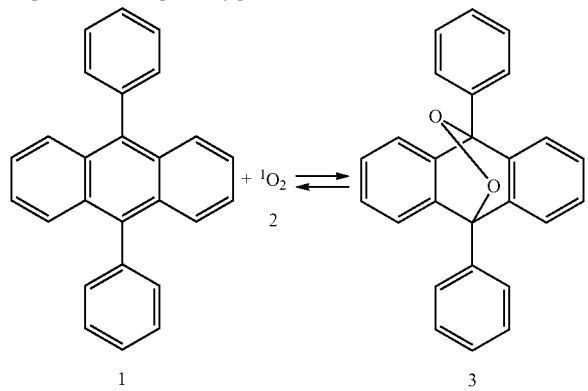

N-substituted-2-pyridones 4 have been reported to trap singlet oxygen upon irradiation in the presence of a photosensitizer to give 1,4-endoperoxides 5. Such photosensitizers comprise, inter alia, substituted porphyrin compounds. These endoperoxides are more efficient in thermally releasing singlet oxygen than the endoperoxide derivatives of PAHs.

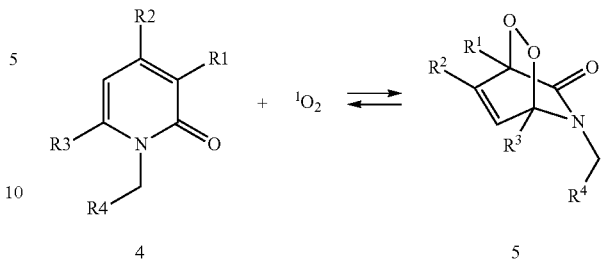

Applicants have prepared and studied compound 4, wherein $R^1$ is selected from the group consisting of H, $CH_3$, $OCH_3$, and $(CH_3)_2N$, wherein $R^2$ is selected from the group consisting of H and $CH_3$, wherein $R^3$ is selected from the group consisting of H, $CH_3$, $OCH_3$, and $(CH_3)_2N$, and, wherein $R^4$ is selected from the group consisting of Ph, p-CNPh, $CH_2(CH_2)_4CH_3$, $COCH_2CH_3$, OH, and COOH. Applicants have found that substituted pyridones 4 comprising electron donating groups $R^1$ and $R^2$ facilitate the reaction with singlet oxygen to form endo peroxide 5.

Applicants have prepared a number of compounds comprising both a porphyrin photocatalyst moiety and one or more pyridone singlet oxygen trap moieties. As those skilled in the art will appreciate, the vapor pressure of a porphyrin compound is several orders of magnitude less than the vapor pressure of a substituted pyridone 4. Covalently bonding one or more pyridone moieties to a porphyrin compound assures that a desired ratio of singlet oxygen traps to singlet oxygen generators is maintained in a coating, solution, formulation, and the like.

More specifically, Applicants have prepared substituted porphyrin compound 140 comprising four 2-pyridone moieties, substituted porphyrin compound 1420 comprising one 2-pyridone moiety, and substituted porphyrin compound 1430 comprising two 2-pyridone moieties.

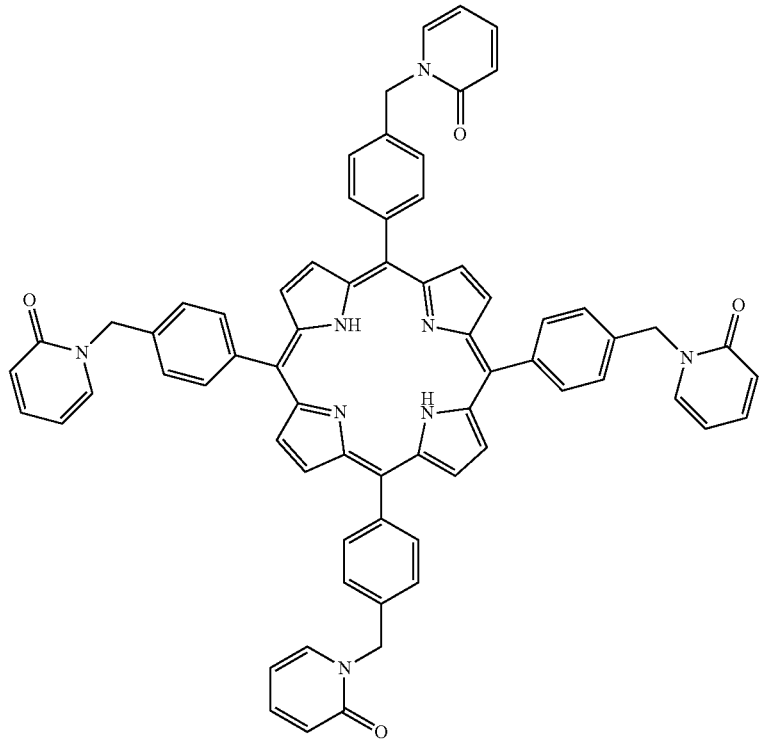

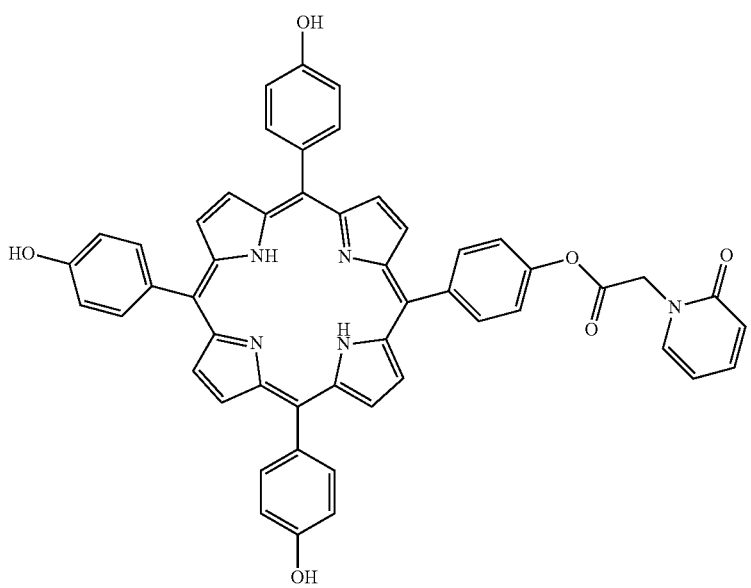

1420

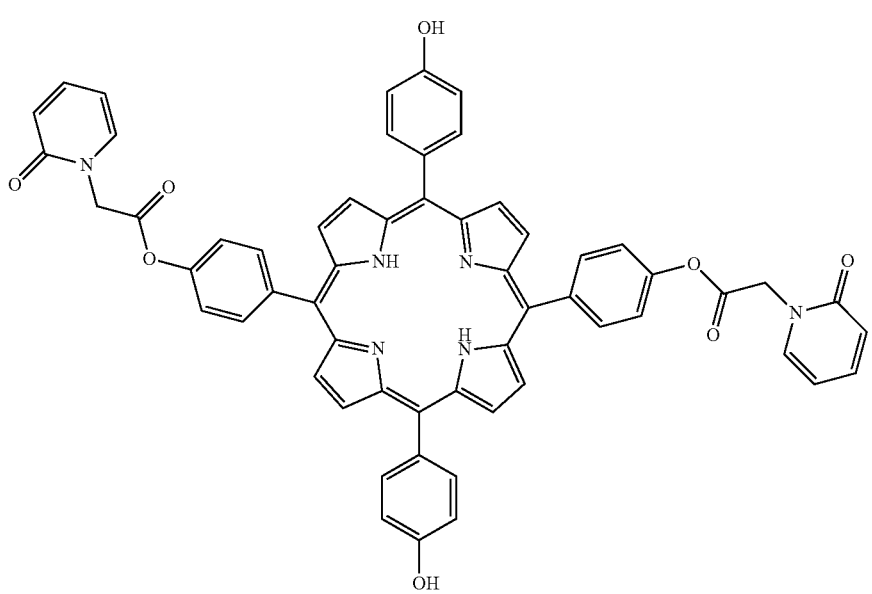 [SMILES: O=C(Cn1ccccc1=O)Oc1ccc(-c2c3nc(c(-c4ccc(O)cc4)c4ccc([nH]4)c(-c4ccc(OC(=O)Cn5ccccc5=O)cc4)c4nc(c(-c5ccc(O)cc5)c5ccc2[nH]5)C=C4)C=C3)cc1]

1430

Figure 2:
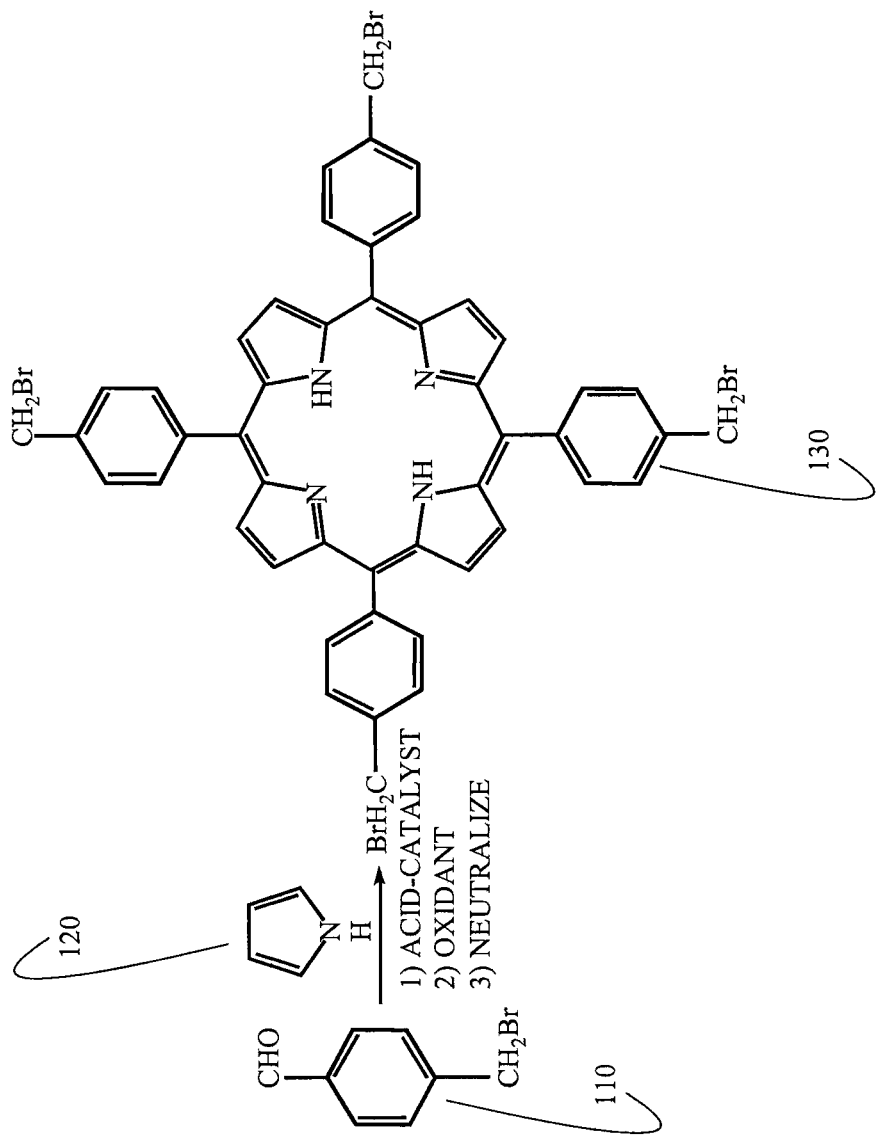
Figure 3:
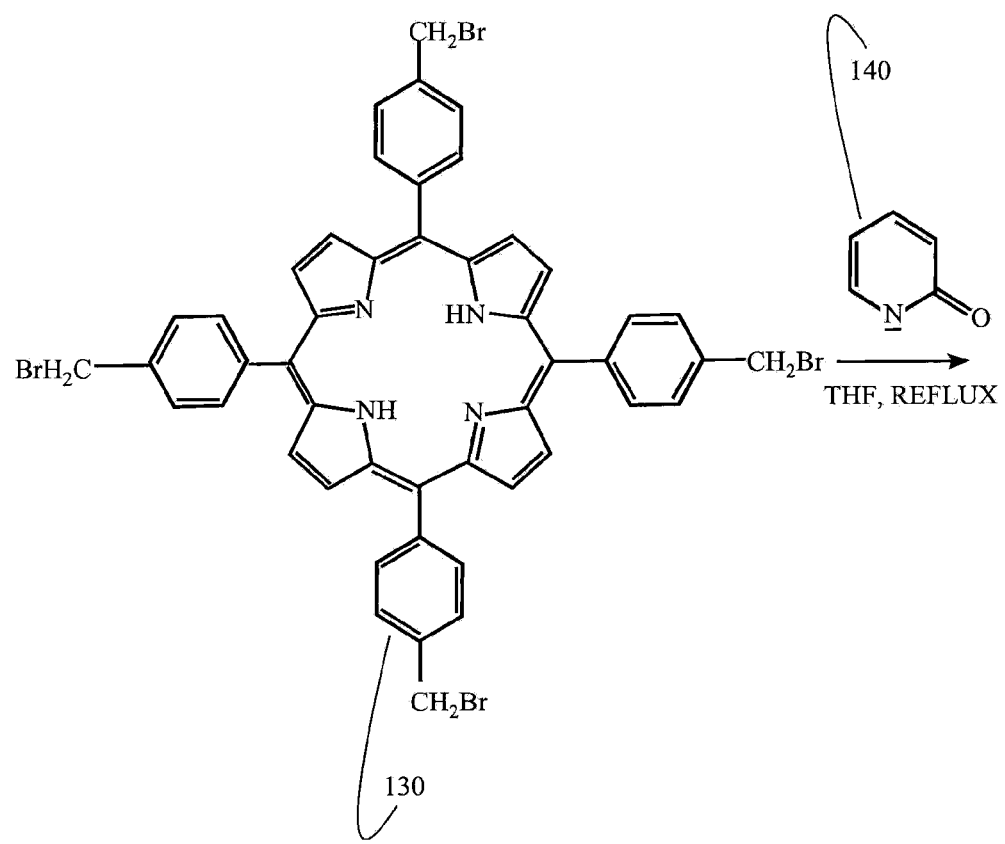

Referring to FIG. 2, porphyrin 130 was prepared from starting materials 110 and 120 utilizing three acid catalysts, namely BF$_3$-etherate, trifluoroacetic acid ("TFA"), and amberlyst ion-exchange resin. Referring to FIG. 3, tetra pyridone substituted porphyrin 140 was prepared from porphyrin 130 as described hereinbelow.

Referring to FIG. 12, porphyrin 1230 was prepared from starting materials 1210 and 120 utilizing propionic anhydride and propionic acid. FIG. 13 shows the $^1$H-NMR spectrum for porphyrin 1230. Referring to FIG. 14, mono- and di-substituted porphyrins 1420 and 1430 were prepared from porphyrin 1230 and substituted pyridone 1410.

The following Examples are presented to further illustrate to persons skilled in the art how to make and use the invention. These examples are not intended as a limitation, however, upon the scope of the invention.

EXAMPLE 1

Preparation of Porphyrin 130

A 500 mL round bottom flask containing p-(α-bromo) methyl benzaldehyde (54; 0.6 g, 3 mmol) and amberlyst resin (4 g) was equipped with a Claisen distilling head, a dropping funnel and a condenser. All open ends were sealed with rubber septa. The glassware was flame-dried under vacuum. Anhydrous chloroform (300 mL) was introduced to the flask via septum. Pyrrole (0.25 mL; 3.5 mmol) was added to the flask by a syringe through septum.

The mixture was stirred at room temperature in the dark under an argon atmosphere for 5 hours. After 10 min addition of pyrrole, the solution mixture was light yellow. Solution color changed during 5 hours reaction period from light yellow to orange to red to dark red and dark. DDQ (0.5 g) was added to the dark solution. The resulting yellowish dark red solution was allowed to stir at room temperature for 1 hour.

The mixture was neutralized with pyridine, and then filtered. The filtrate was collected and concentrated to give black solid residue. The solid residue was analyzed by TLC and $^1$H-NMR. TLC analysis (100% DCM) shows two purple components at $R_{fs}$ of 0.9 and 0.5 and a greenish yellow at the base line. The $^1$H-NMR spectrum (CDCl$_3$) of this solid residue revealed a characteristic porphyrin N-H at δ −2.81. This indicates that this crude solid contained a porphyrin. The solid residue (0.6 g) was subjected to a column chromatography (100% DCM). The two purple bands were collected and concentrated to give purple solids (70 mg and 40 mg). The purple solids were analyzed by $^1$H-NMR.

Figure 4A:
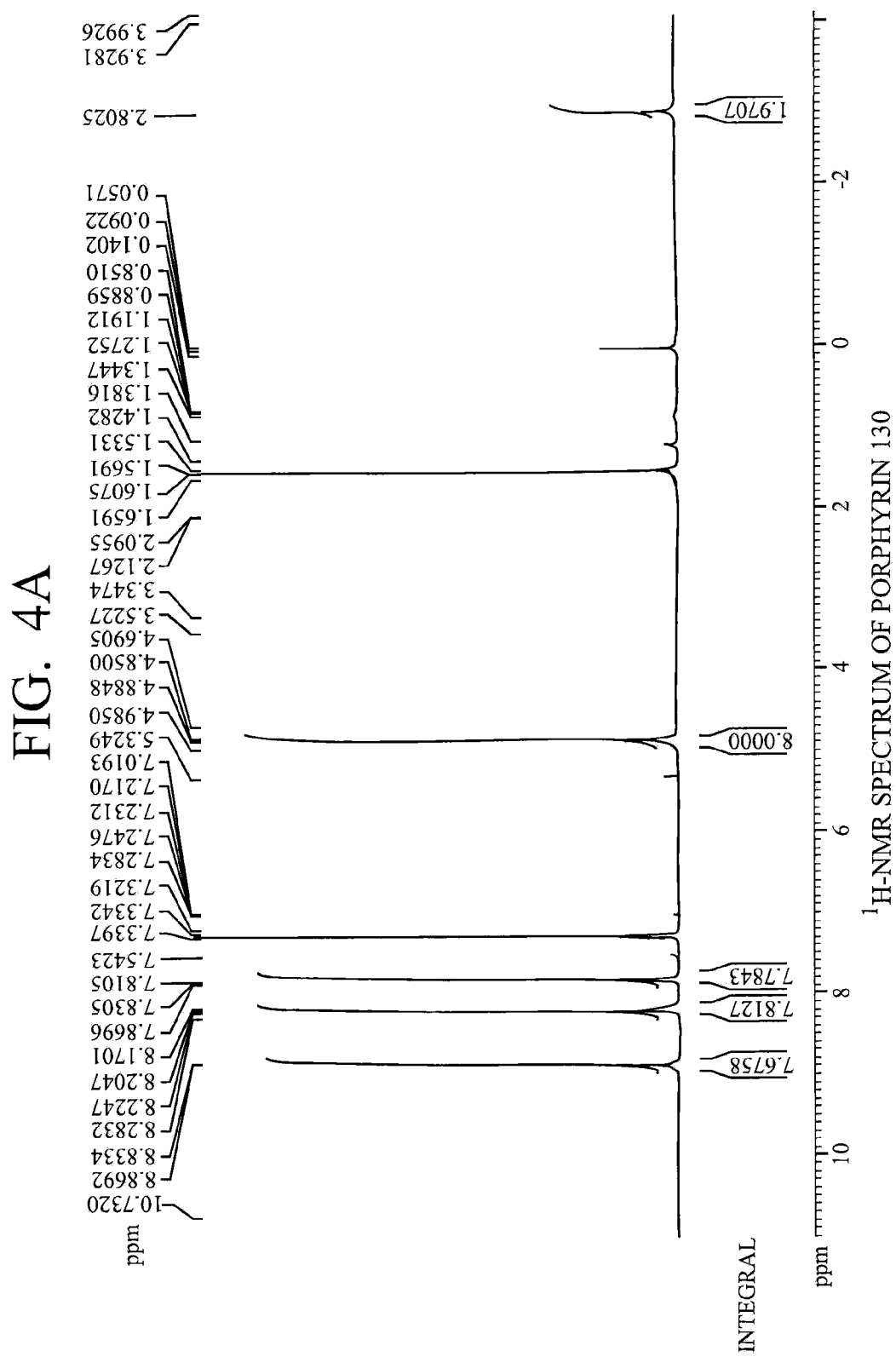

FIG. 4A comprises the $^1$H-NMR spectrum for porphyrin 130, i.e. the first eluted purple band, and shows a broad singlet (2H) upfield at δ −2.81 which is a characteristic absorption of the porphyrin N-H. The downfield singlet (8H) at δ 8.86 corresponds to pyrrolic protons of porphyrin. The ortho- and meta-phenyl ring protons appears at δ 7.82 (8H, d; J=8.08 Hz) and δ 8.21 (8H, d; J=8.08 Hz), respectively. The singlet (8H) at δ 4.85 corresponds to the methylene protons.

EXAMPLE 2

Preparation of Porphyrin 140

A 50 mL round bottom flask containing NaH (60%; 0.012 g, 0.3 mmol) was equipped with a Claisen distilling head and a condenser. All open ends were sealed with rubber septa. The glassware was flame-dried under vacuum. A solution of 2-hydroxypyridine (0.025 g, 0.2 mmol) in THF (anh) 7 mL was introduced to the flask by a syringe through septum. The mixture was stirred under argon purge until gas evolution ceased. A solution of the porphyrin 130 (50 mg, 0.05 mmol) in THF (anh) 10 mL was introduced to the flask by a syringe through septum. The resulting purple mixture was stirred and heated under an argon atmosphere at refluxing THF for 4 hours. The reaction mixture was cooled to room temperature. The mixture was filtered. The solid residue was washed by dichloromethane. The dark purple filtrate was collected and concentrated to give a yellowish purple solid. The solid was washed by MeOH twice to give a purple solid (40 mg). The purple solid was analyzed by $^1$H-NMR and UV-Vis absorption spectroscopy.

Figure 4B:
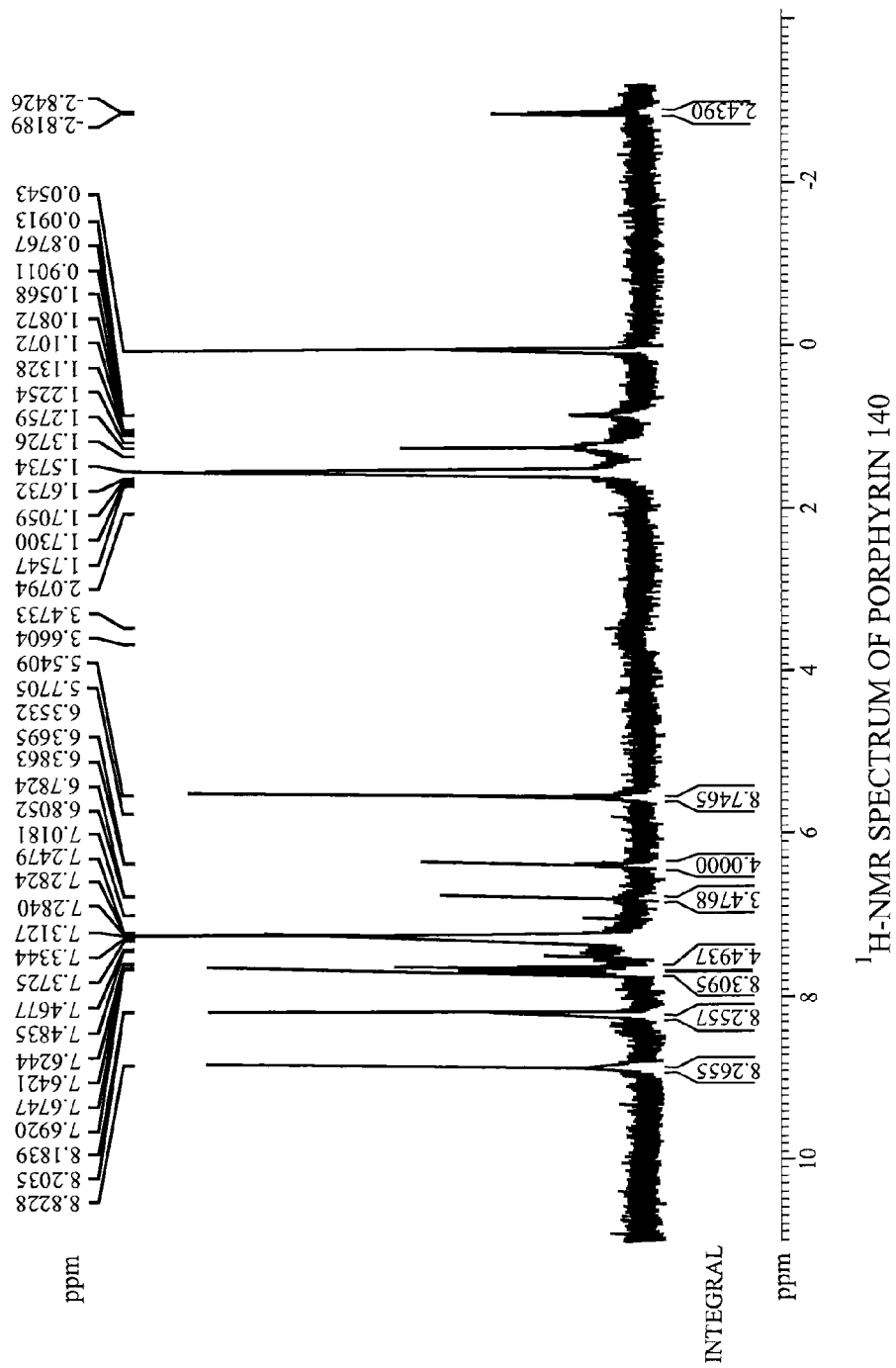

FIG. 4B comprises the $^1$H-NMR spectrum for porphyrin 140, and shows a broad singlet (2H) upfield at δ −2.81 which is a characteristic absorption of the porphyrin N-H. The most downfield singlet (8H) at δ 8.82 is assigned to the pyrrolic protons. The two doublets at δ 7.68 (8H, d; J=7.58 Hz) and δ 8.19 (8H, d; J=7.58 Hz) correspond to the ortho- and meta-phenyl ring protons of the porphyrin, respectively. The absorptions at δ 6.37 (t, 4H; J=6.82 Hz), 6.79 (d, 4H; J=9.09 Hz), 7.48 (t, 4H; J=9.09 Hz) and 7.63 (d, 4H; J=6.82 Hz) are due to the pyridone ring protons.

The key signal is a singlet at δ 5.54 (8H) which corresponds to the methylene protons. If this sample was only a mixture of the porphyrin 130 and 2-pyridone, the singlet, which is due to the methylene protons of the porphyrin 130, would appear at δ 4.85. This spectrum clearly shows that the methylene protons resonance shifts downfield to δ 5.54 which corresponds to the methylene protons attached to a phenyl ring and a nitrogen atom of the pyridone ring as previously observed from N-benzyl-2-pyridone. Therefore, the $^1$H-NMR spectrum suggests that this porphyrin is covalently linked to 2-pyridone. No singlet at δ 4.85 is observed suggesting that 2-pyridone is covalently linked to all four methylene carbons of the porphyrin.

Figure 5:
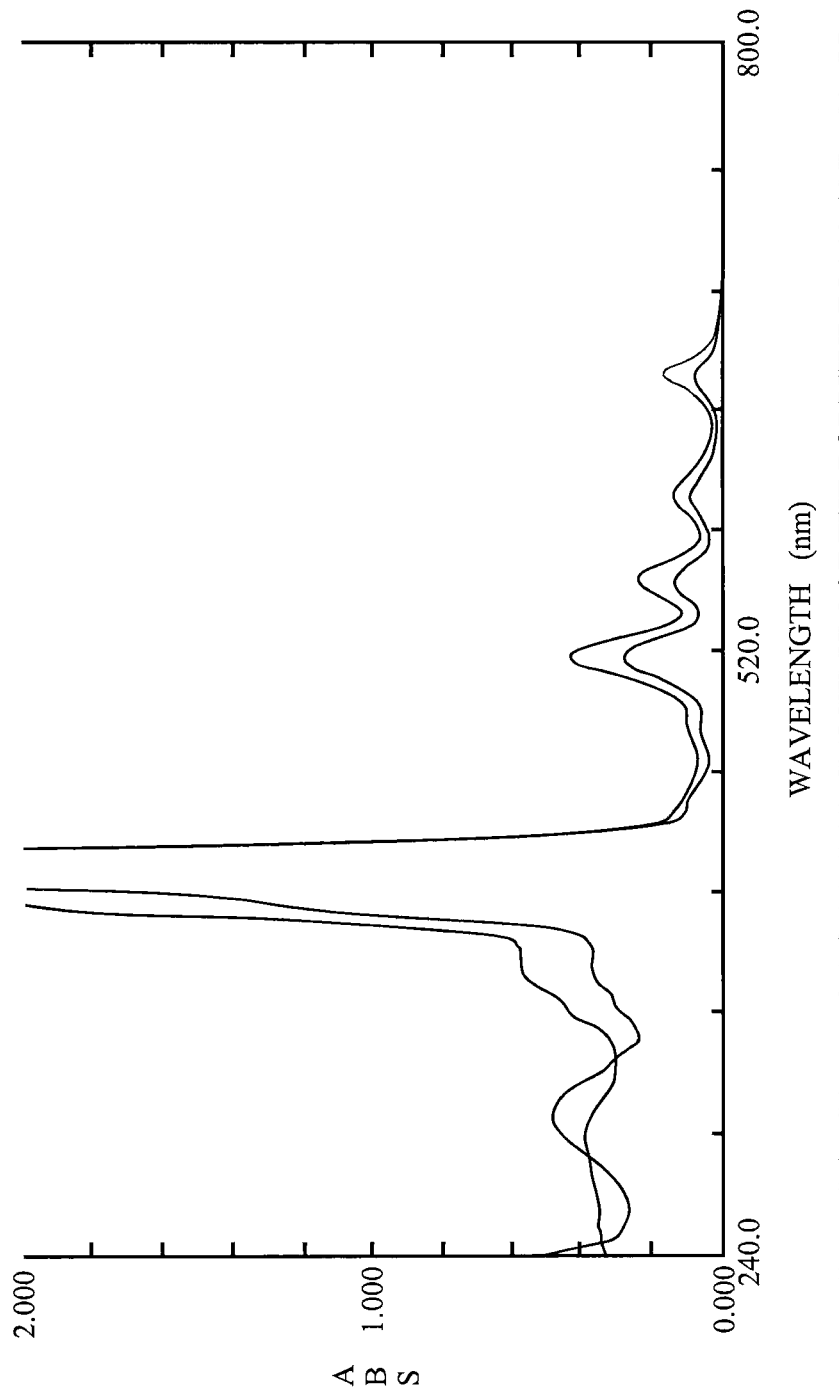

FIG. 5 shows an UV-Vis absorption overlay spectrum between the porphyrin 140 and tetra-(4-methylphenyl)porphyrin ("T4mPP"), compound 6, in chloroform solvent.

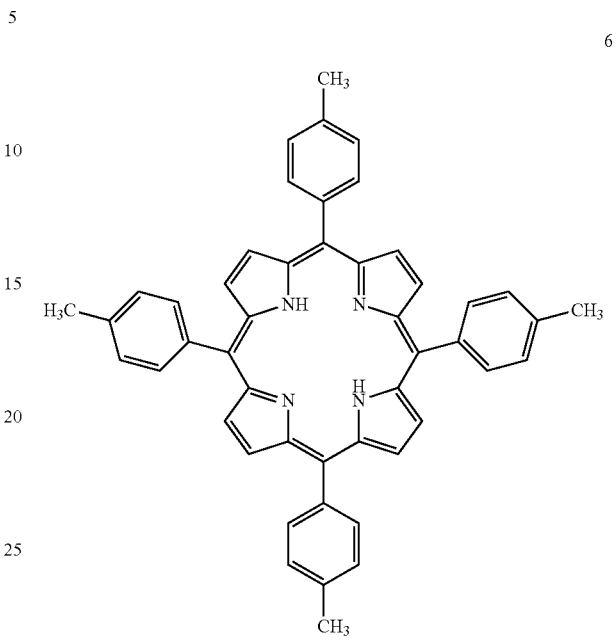

6

Figure 6:
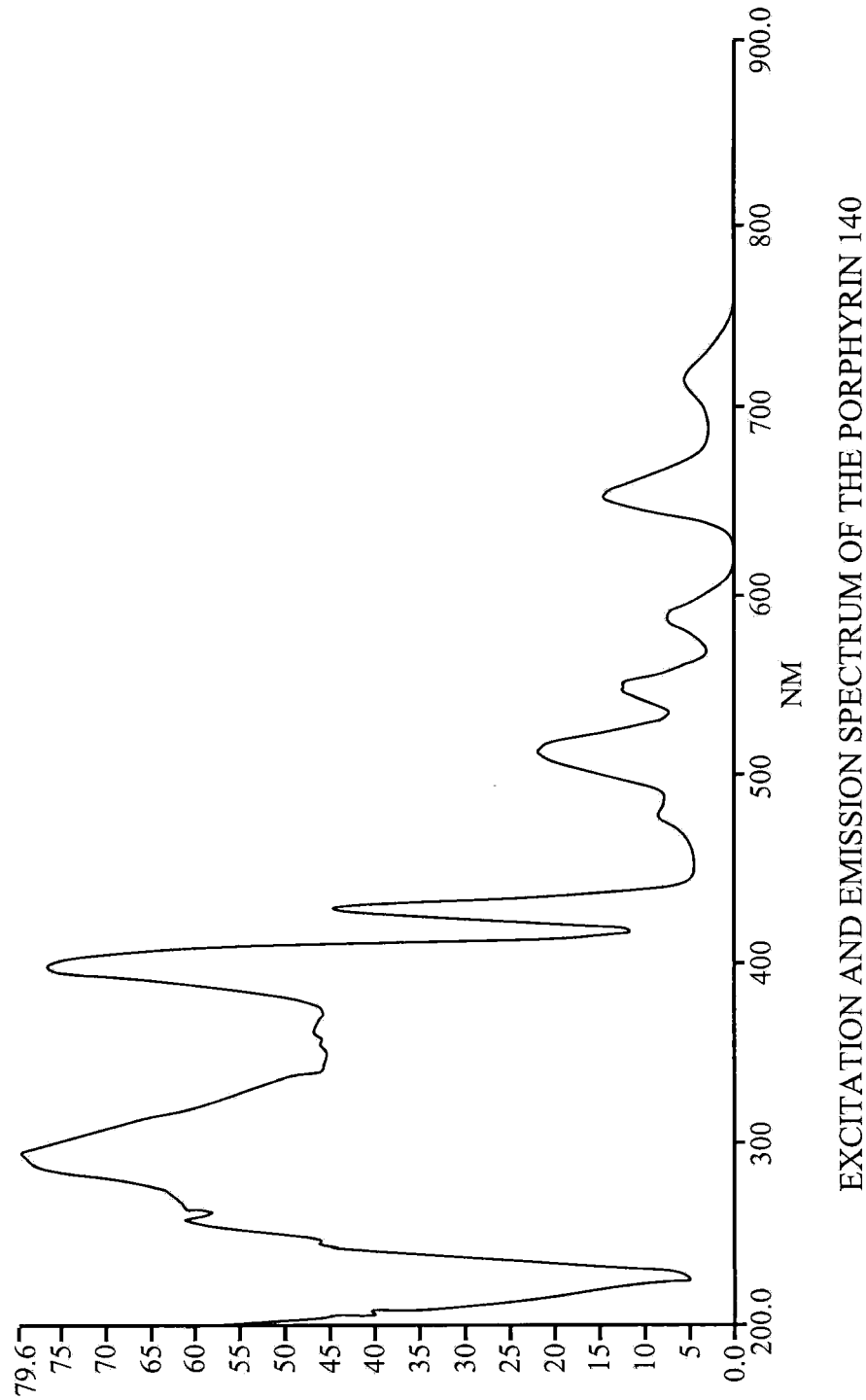

The spectrum reveals that pyridone linkage does not perturb the excited state of the porphyrin. The fluorescence emission of the porphyrin 140 shown in FIG. 6 was similar to the emission of T4mPP.

Solutions of the porphyrin 140 and T4mPP were irradiated through a Pyrex or a yellow filter and monitored by UV-Vis absorption spectroscopy. The solution was purged with a continuous fine steam oxygen gas during irradiation.

In addition, solutions of porphyrin 140 (2.4 mg), T4mPP (0.6 mg)+N-benzyl-2-pyridone (10 mg), and T4mPP (0.6 mg) in CDCl$_3$ (1 mL) were irradiated through a Pyrex filter or a yellow filter. The solutions were purged with a continuous fine steam oxygen gas during irradiation. These solutions were analyzed by $^1$H-NMR. The final solutions containing pyridone were heated at 50° C. for 30 min and analyzed by $^1$H-NMR.

Figure 7:
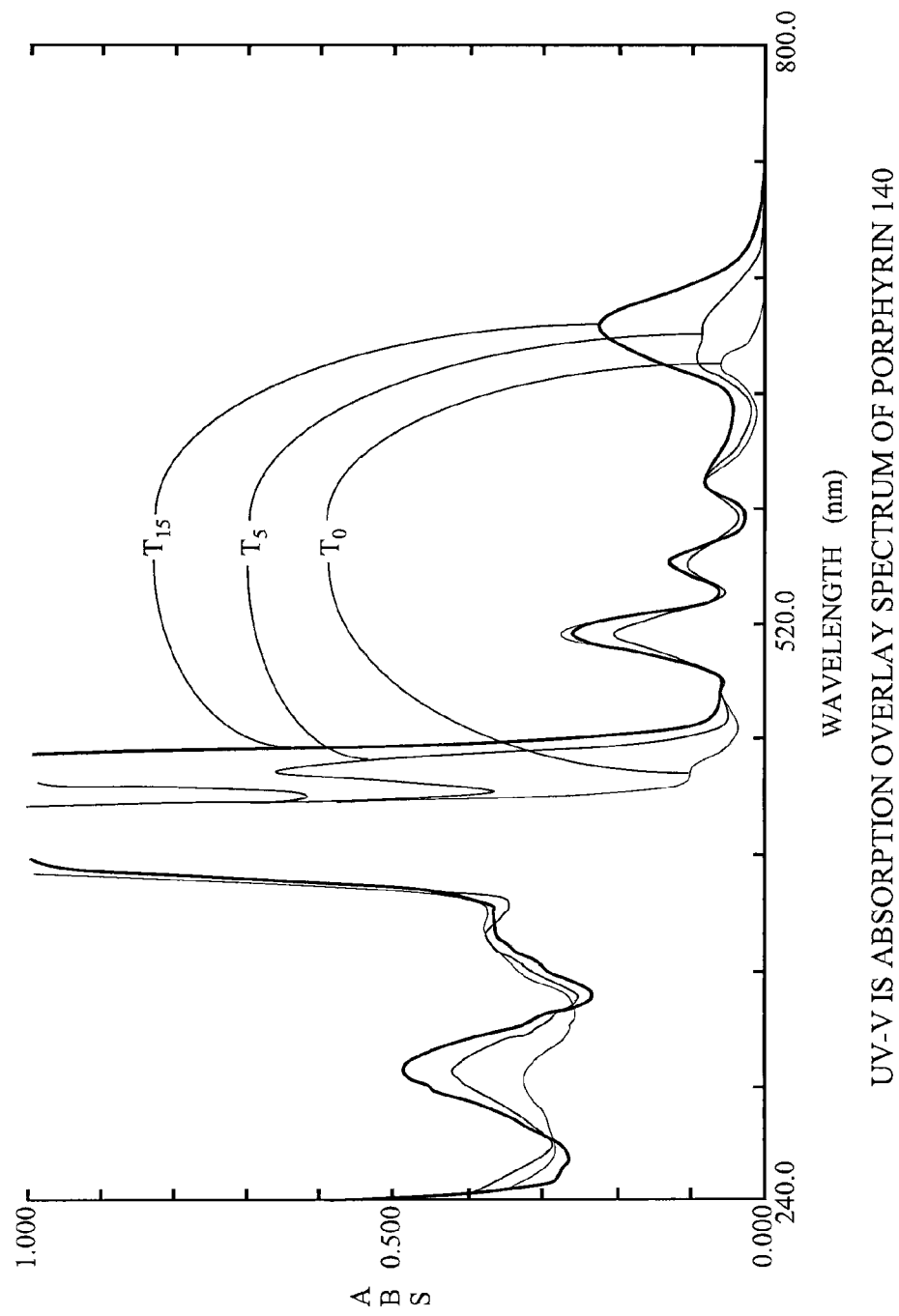
Figure 8:
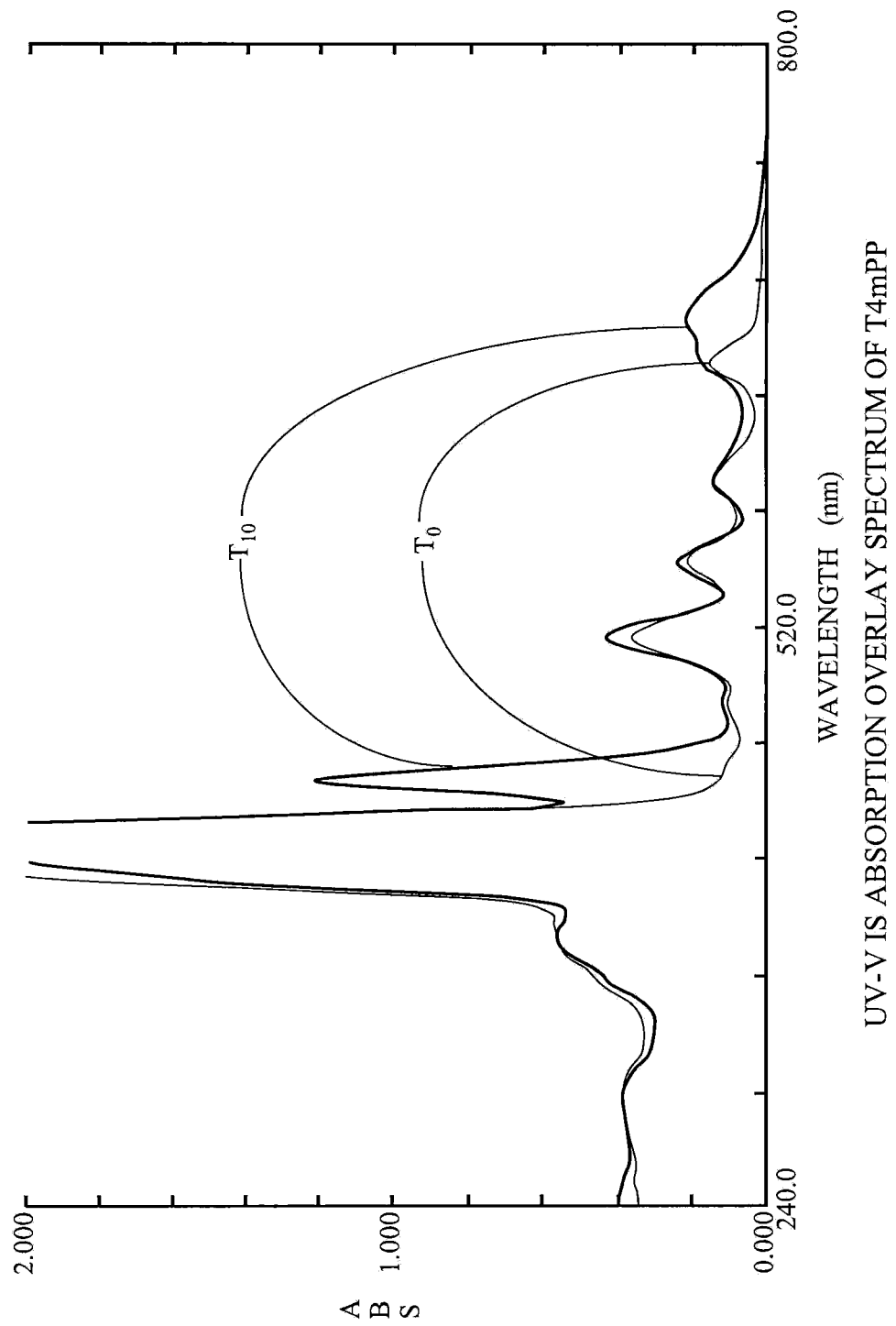

Irradiation of diluted solutions of the porphyrin 140 and T4mPP in chloroform through a Pyrex filter results in change of solution color from weak purple to yellow. FIG. 7 shows an UV-Vis absorption overlay spectrum of the porphyrin 140 solution in chloroform before and after 5 and 15 min of irradiation. FIG. 8 shows an UV-Vis absorption overlay spectrum of a solution of T4mPP in chloroform before and after 10 min of irradiation. FIGS. 7 and 8 demonstrate that the efficiency of porphyrin 140 as a photocatalyst is not diminished by the presence of the 4 pyridone moieties.

Figure 9:
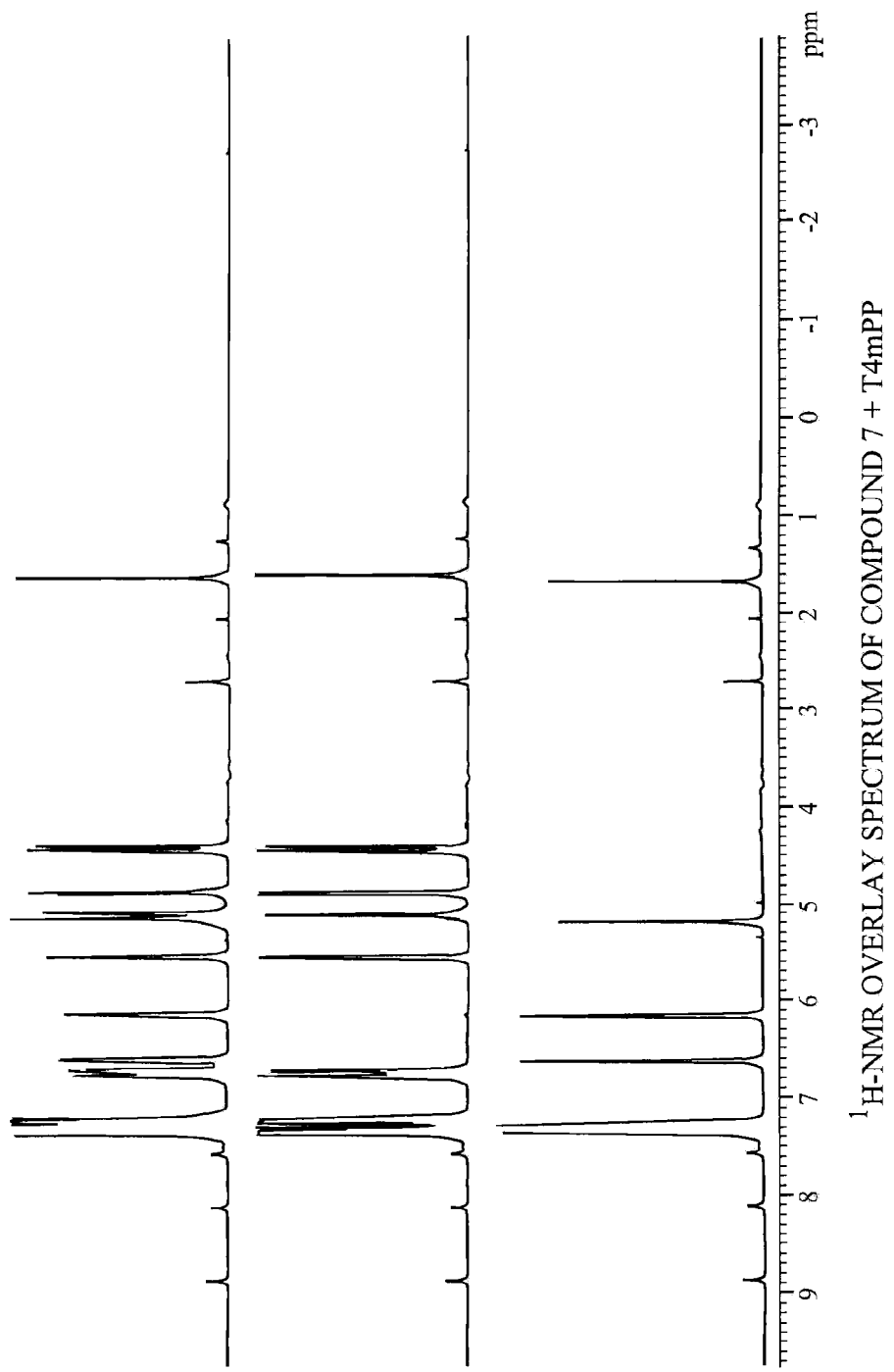
FIG. 9 shows the $^1$H-NMR overlay spectrum of T4mPP+ N-benzyl-2-pyridone in solution before and after 120 min of irradiation through a yellow filter.

FIG. 9 comprises a $^1$H-NMR overlay spectrum of T4mPP+ N-benzyl-2-pyridone, compound 7, in solution before and after 120 min of irradiation through a yellow filter. The spectrum reveals more than 99% consumption of 7, and the formation of a product which has previously been suggested as the endoperoxide 8. After 120 min of irradiation, the spectrum does not reveal a sign of a photoproduct formed from T4mPP as well as color change which were observed when only T4mPP in CDCl$_3$ was irradiated for 10 min through a Pyrex filter. Thus, this suggests that T4mPP is photostable toward irradiation at λ>500 nm. Quantitative analysis of irradiation of T4mPP+7 in CDCl$_3$ is shown in Table 2.

TABLE 2

¹H-NMR quantitative analysis of the irradiation of 7 + T4mPP

7 + T4mPP (¹H-integration)

| Time (min) | —CH₂— SM | av Dias•H-P | Relative ratio |
|---|---|---|---|
| 0 | — | — | — |
| 10 | 2.0 | 0.48 | 0.32 |
| 20 | 1.96 | 1.1 | 0.53 |
| 30 | 2.05 | 2.74 | 0.73 |
| 50 | 2.1 | 19.2 | 0.95 |
| 120 | — | — | >0.99 |
| Heated at 50° C. for 30 min | | | |
| 30 | 2.02 | 1.03 | 0.5 |

The data of Table 2 were calculated using Equations (1), (2), and (3).

Relative ratio of product amount=(P)/[(SM/2)=P]  (1)

in the mixture SM/2=−CH₂ integration of SM/2  (2)

Percent consumption=Relative Ratio Of Product×100  (3)

Table 2 shows that 7 is >90% consumed after 50 min of irradiation. By comparison with the irradiation using aluminum phthalocyanine ("AlPc") sensitizer, the relative ration of the endoperoxide 8 formation was observed at 0.08 after 160 min of irradiation while in the reaction with T4mPP sensitizer the ratio is >0.99 after 120 min of irradiation. This result indicates that T4mPP is approximately twelve times more effective than AlPc for sensitized singlet oxygen generation.

Figure 10:
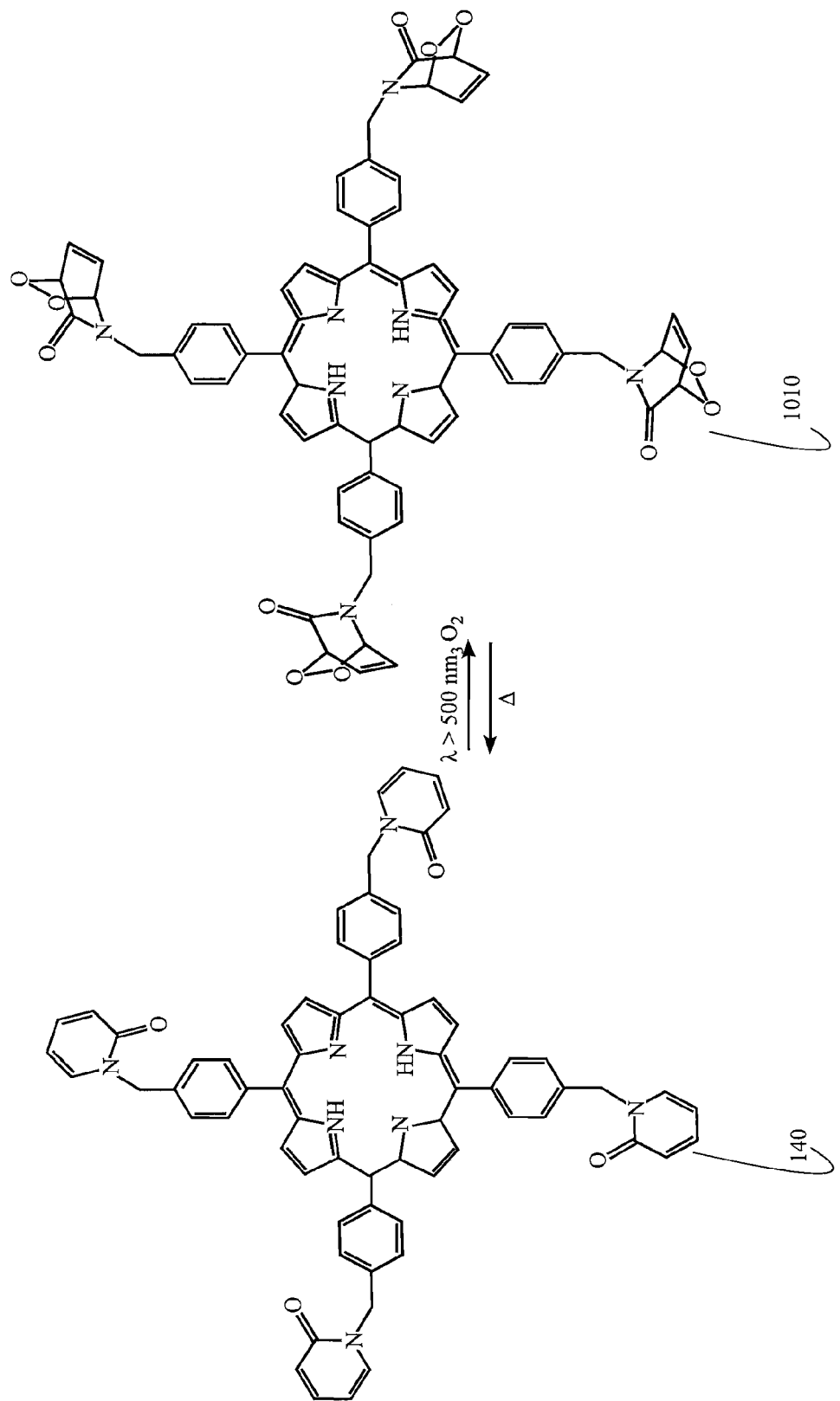
FIG. 10 shows the reversible chemical reaction of pyridone/porphyrin 140 with singlet oxygen to form tetra-endoperoxide 1010.

FIG. 10 shows the reversible reaction of pyridone/porphyrin 140 with singlet oxygen to form tetra-endoperoxide 1010. FIG. 11A comprises a ¹H-NMR overlay spectrum of the porphyrin 140 solution in CDCl₃ before and after irradiation through a yellow filter. Twenty minute irradiations followed by 30 minute heatings were carried out in three cycles. Curve 1110 shows the initial sample. Curve 1120 shows the sample after a first 20 minute irradiation.

Curve 1130 shows sample after a first 20 minute irradiation and a first 30 minute heating. Curve 1140 shows the sample after a first irradiation, a first 30 minute heating, and a second 20 minute irradiation. Curve 1150 shows the sample after a first irradiation, a first 30 minute heating, a second 20 minute irradiation, and a second 30 minute heating. Curve 1160 shows the sample after a first irradiation, a first 30 minute heating, a second 20 minute irradiation, a second 30 minute heating, and a third 20 minute irradiation. Curve 1170 shows the sample after a first irradiation, a first 30 minute heating, a second 20 minute irradiation, a second 30 minute heating, a third 20 minute irradiation, and a third 30 minute heating. The solution in curve 1180 was further irradiated for 60 min.

After irradiation for 20 min in the first cycle, the spectrum reveals the decrease in integrations of the methylene protons and the pyridone ring protons and reveals formation of new proton signals at δ 4.89 (d; J=16.0 Hz), 5.19 (d; J=16.0 Hz), 5.25 (d; J=6.0 Hz), 5.96 (d; J=4.8 Hz), 6.95 (m), and 7.01 (m).

The two new doublets appear in the region of δ 4.5-5.5, which are associated with large coupling constants, are characteristic absorptions indicating the formation of an endoperoxide derivative formed from singlet oxygen trapping of 2-pyridones. These new signal integrations are decreased after heating at 50° C. for 30 min while the intensities of the methylene protons and pyridone ring protons increase. These results correspond to the previously observed sensitized trapping and thermal reverse releasing singlet oxygen from 2-pyridones.

Referring to FIG. 11B, graph 1100 graphically recites thermolysis data for porphyrin endoperoxide 1010, Referring now to FIG. 11C, graph 1105 illustrates 1/T Vs ln(k/T) from the thermolysis of the porphyrin endoperoxide 1010. FIG. 16A comprises a ¹H-NMR overlay spectrum of the porphyrins 1430 and 1440 solution in CDCl₃ before and after irradiation through a yellow filter. Ninety minute irradiations followed by 30 minute heatings were carried out in two cycles. Curve 1610 shows the initial sample. Curve 1620 shows the sample after a first 90 minute irradiation.

Curve 1630 shows sample after a first 90 minute irradiation and a first 30 minute heating. Curve 1640 shows the sample after a first irradiation, a first 30 minute heating, and a second 90 minute irradiation. Curve 1650 shows the sample after a first irradiation, a first 30 minute heating, a second 90 minute irradiation, and a second 30 minute heating.

Referring to FIG. 16B, graph 1600 graphically recites thermolysis data for porphyrin endoperoxides formed from the mixture of pyridone/porphyrins 1430 and 1440. Referring now to FIG. 16C, graph 1605 illustrates 1/T Vs ln(k/T) from the thermolysis of the porphyrin endoperoxides formed from the mixture of pyridone/porphyrins 1430 and 1440. FIG. 17 comprises Table 17 which recites kinetic decomposition data for porphyrins 140 mixture 1430 and 1440, and the endoperoxides formed therefrom. While the preferred embodiments of the present invention have been illustrated in detail, it should be apparent that modifications and adaptations to those embodiments may occur to one skilled in the art without departing from the scope of the present invention.

I claim:
1. A compound according to the structure

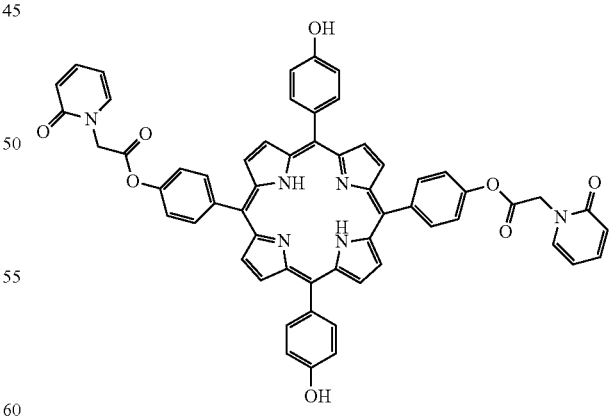

or a salt thereof.